United States Patent [19]

Metz et al.

[11] Patent Number: 5,370,996

[45] Date of Patent: Dec. 6, 1994

[54] FATTY ACYL REDUCTASES

[75] Inventors: James G. Metz, Woodland, Calif.; Michael R. Pollard, Madison, Wis.; Michael W. Lassner, Davis, Calif.

[73] Assignee: Calgene, Inc., Davis, Calif.

[21] Appl. No.: 920,430

[22] Filed: Jul. 31, 1992

Related U.S. Application Data

[63] Continuation-in-part of Ser. No. 796,256, Nov. 20, 1991, abandoned, and Ser. No. 767,251, Sep. 27, 1991, and Ser. No. 659,975, Feb. 22, 1991, abandoned.

[51] Int. Cl.⁵ .................. C12P 21/00; C12P 7/64; C12N 5/00; C07H 21/04
[52] U.S. Cl. ................. 435/69.1; 435/240.4; 435/134; 435/71.2; 435/70.1; 435/252.3; 435/252.33; 435/320.1; 435/172.3; 536/23.2; 536/23.6
[58] Field of Search ............. 435/172.3, 320.1, 69.1, 435/71.1, 71.2, 134, 240.4, 252.3; 536/27, 23.2, 23.6; 935/66, 67, 72, 9, 14; 800/205, 250

[56] References Cited

U.S. PATENT DOCUMENTS 4,394,443 7/1983 Weissman et al. .................. 435/68

FOREIGN PATENT DOCUMENTS 0255378 2/1988 European Pat. Off. ...... C12N 15/00

OTHER PUBLICATIONS

Gunstone, F. Endeavor, New Series, vol. 14 (1990) pp. 1–4 of reprint.
G. Wildner et al. (abstract) Southwes Consorium on Plant Genetics and Water Resources (Apr. 22–24, 1990) New Mexico.
P. Kolattukudy et al. Meth. Enzymol., vol. 71 ('81) pp. 263–275.
R. Moreau et al. Arch. Biochem. Biophys., vol. 194 ('79) pp. 422–430.
J. Ohlrogge et al. Lipids, vol. 13 ('78) pp. 203–210.
T. Wolfrum et al. Int. J. of Systematic Bacteriol., vol. 36 ('86) pp. 24–28, Pushnik, J., et al. (abstract), 4th Mtg.
M. Pollard et al. Lipids, vol. 14 ('79) pp. 651–662.
J. van Renswonde et al. Meth. Enzymol., vol. 104 ('84) pp. 329–339.
R. Achersold et al. PNAS, vol. 84 ('87) pp. 6970–6974.
A. Lloyd et al. Science, vol. 234 ('86) pp. 464–466.
A. Shatzman et al. Meth. Enzymol., vol. 152 ('87) pp. 661–673.
X.-Y. Wu et al. Lipids, vol. 16 ('81) pp. 897–902.

Primary Examiner—David T. Fox
Assistant Examiner—Charles Rories

[57] ABSTRACT

By this invention, a partially purified seed-plant fatty acyl reductase protein is provided, wherein said protein is active in the formation of a fatty alcohol from a fatty acyl substrate. Of special interest are jojoba embryo reductase proteins having molecular mass of about 54 and 52 kD and sequences obtainable therefrom. Also considered are amino acid and nucleic acid sequences obtainable from such fatty acyl reductases, which sequences may be used for preparation of recombinant constructs useful for expression of reductase in host cells, which results in the production of fatty alcohols in said cells.

26 Claims, 6 Drawing Sheets

```
AAATCCTCCA CTCATACACT CCACTTCTCT CTCTCTCTCT CTCTCTCTGA AACAATTGA         60

GTAGCAAACT TAAAAGAAA ATG GAG GAA ATG GGA AGC ATT TTA GAG TTT CTT        112
                     Met Glu Glu Met Gly Ser Ile Leu Glu Phe Leu
                       1                   5                  10

GAT AAC AAA GCC ATT TTG GTC ACT GGT GCT ACT GGC TCC TTA GCA AAA         160
Asp Asn Lys Ala Ile Leu Val Thr Gly Ala Thr Gly Ser Leu Ala Lys
             15                  20                  25

ATT TTT GTG GAG AAG GTA CTG AGG AGT CAA CCG AAT GTG AAG AAA CTC         208
Ile Phe Val Glu Lys Val Leu Arg Ser Gln Pro Asn Val Lys Lys Leu
         30                  35                  40

TAT CTT CTT TTG AGA GCA ACC GAT GAC GAG ACA GCT GCT CTA CGC TTG         256
Tyr Leu Leu Leu Arg Ala Thr Asp Asp Glu Thr Ala Ala Leu Arg Leu
 45                  50                  55                  60

CAA AAT GAG GTT TTT GGA AAA GAG TTG TTC AAA GTT CTG AAA CAA AAT         304
Gln Asn Glu Val Phe Gly Lys Glu Leu Phe Lys Val Leu Lys Gln Asn
             65                  70                  75
```

FIG. 1A

```
TTA GGT GCA AAT TTC TAT TCC TTT GTA TCA GAA AAA GTG ACT GTA GTA      352
Leu Gly Ala Asn Phe Tyr Ser Phe Val Ser Glu Lys Val Thr Val Val
         80                  85                  90

CCC GGT GAT ATT ACT GGT GAA GAC TTG TGT CTC AAA GAC GTC AAT TTG      400
Pro Gly Asp Ile Thr Gly Glu Asp Leu Cys Leu Lys Asp Val Asn Leu
         95                 100                 105

AAG GAA GAA ATG TGG AGG GAA ATC GAT GTT GTT AAT CTA GCT GCT          448
Lys Glu Glu Met Trp Arg Glu Ile Asp Val Val Asn Leu Ala Ala
        110                 115                 120

ACA ATC AAC TTC ATT GAA AGG TAC GAC GTG TCT CTG CTT ATC AAC ACA      496
Thr Ile Asn Phe Ile Glu Arg Tyr Asp Val Ser Leu Leu Ile Asn Thr
        125                 130                 135                 140

TAT GGA GCC AAG TAT GTT TTG GAC TTC GCG AAG AAG TGC AAC AAA TTA      544
Tyr Gly Ala Lys Tyr Val Leu Asp Phe Ala Lys Lys Cys Asn Lys Leu
        145                 150                 155

AAG ATA TTT GTT CAT GTA TCT ACT GCT TAT GTA TCT GGA GAG AAA AAT      592
Lys Ile Phe Val His Val Ser Thr Ala Tyr Val Ser Gly Glu Lys Asn
        160                 165                 170
```

FIG. 1B

```
GGG TTA ATA CTG GAG AAG CCT TAT ATG GGC GAG TCA CTT AAT GGA        640
Gly Leu Ile Leu Glu Lys Pro Tyr Met Gly Glu Ser Leu Asn Gly
            175             180             185

AGA TTA GGT CTG GAC ATT AAT GTA GAG AAG AAA CTT GTG GAG GCA AAA    688
Arg Leu Gly Leu Asp Ile Asn Val Glu Lys Lys Leu Val Glu Ala Lys
        190             195             200

ATC AAT GAA CTT CAA GCA GCG GGG GCA ACG GAA AAG TCC ATT AAA TCG    736
Ile Asn Glu Leu Gln Ala Ala Gly Ala Thr Glu Lys Ser Ile Lys Ser
205             210             215             220

ACA ATG AAG GAC ATG GGC ATC GAG AGG GCA AGA CAC TGG GGA TGG CCA    784
Thr Met Lys Asp Met Gly Ile Glu Arg Ala Arg His Trp Gly Trp Pro
            225             230             235

AAT GTG TAT GTA TTC ACC AAG GCA TTA GGG GAG ATG CTT TTG ATG CAA    832
Asn Val Tyr Val Phe Thr Lys Ala Leu Gly Glu Met Leu Leu Met Gln
            240             245             250

TAC AAA GGG GAC ATT CCG CTT ACT ATT ATT CGT CCC ACC ATC ATC ACC    880
Tyr Lys Gly Asp Ile Pro Leu Thr Ile Ile Arg Pro Thr Ile Ile Thr
        255             260             265
```

FIG. 1C

```
AGC ACT TTT AAA GAG CCC TTT CCT GGT TGG GTT GAA GGT GTC AGG ACC    928
Ser Thr Phe Lys Glu Pro Phe Pro Gly Trp Val Glu Gly Val Arg Thr
270                         275                 280

ATC GAT AAT GTA CCT GTA TAT TAT GGT AAA GGG AGA TTG AGG TGT ATG    976
Ile Asp Asn Val Pro Val Tyr Tyr Gly Lys Gly Arg Leu Arg Cys Met
    285                 290                 295             300

CTT TGC GGA CCC AGC ACA ATA ATT GAC CTG ATA CCG GCA GAT ATG GTC   1024
Leu Cys Gly Pro Ser Thr Ile Ile Asp Leu Ile Pro Ala Asp Met Val
        305                 310                 315

GTG AAT GCA ACG ATA GTA GCC ATG GTG GCG CAC GCA AAC CAA AGA TAC   1072
Val Asn Ala Thr Ile Val Ala Met Val Ala His Ala Asn Gln Arg Tyr
            320                 325                 330

GTA GAG CCG GTG ACA TAC CAT GTG GGA TCT TCA GCG GCG AAT CCA ATG   1120
Val Glu Pro Val Thr Tyr His Val Gly Ser Ser Ala Ala Asn Pro Met
                335                 340                 345

AAA CTG AGT GCA TTA CCA GAG ATG GCA CAC CGT TAC TTC ACC AAG AAT   1168
Lys Leu Ser Ala Leu Pro Glu Met Ala His Arg Tyr Phe Thr Lys Asn
350                 355                 360
```

FIG. 1D

```
CCA TGG ATC AAC CCG GAT CGC AAC CCA GTA CAT GTG GGT CGG GCT ATG   1216
Pro Trp Ile Asn Pro Asp Arg Asn Pro Val His Val Gly Arg Ala Met
365                 370                 375                 380

GTC TTC TCC TTC TCC ACC TTC CAC CTT TAT CTC ACC CTT AAT TTC       1264
Val Phe Ser Ser Phe Ser Thr Phe His Leu Tyr Leu Thr Leu Asn Phe
        385                 390                 395

CTC CTT CCT TTG AAG GTA CTG GAG ATA GCA AAT ACA ATA TTC TGC CAA   1312
Leu Leu Pro Leu Lys Val Leu Glu Ile Ala Asn Thr Ile Phe Cys Gln
400                 405                 410

TGG TTC AAG GGT AAG TAC ATG GAT CTT AAA AGG AAG ACG AGG TTG TTG   1360
Trp Phe Lys Gly Lys Tyr Met Asp Leu Lys Arg Lys Thr Arg Leu Leu
        415                 420                 425

TTG CGT TTA GTA GAC ATT TAT AAA CCC TAC CTC TTC TTC CAA GGC ATC   1408
Leu Arg Leu Val Asp Ile Tyr Lys Pro Tyr Leu Phe Phe Gln Gly Ile
430                 435                 440

TTT GAT GAC ATG AAC ACT GAG AAG TTG CGG ATT GCT GCA AAA GAA AGC   1456
Phe Asp Asp Met Asn Thr Glu Lys Leu Arg Ile Ala Ala Lys Glu Ser
445                 450                 455                 460
```

FIG. 1E

```
ATA GTT GAA GCT GAT ATG TTT TAC TTT GAT CCC AGG GCA ATT AAC TGG   1504
Ile Val Glu Ala Asp Met Phe Tyr Phe Asp Pro Arg Ala Ile Asn Trp
            465                     470                     475

GAA GAT TAC TTC TTG AAA ACT CAT TTC CCA GGN GTC GTA GAG CAC GTT   1552
Glu Asp Tyr Phe Leu Lys Thr His Phe Pro Gly Val Val Glu His Val
            480                     485                     490

CTT AAC TAAAAGTTAC GGTACGAAAA TGAGAAGATT GGAATGCATG CACCGAAAGN   1608
Leu Asn

NCAACATAAA AGACGTGGTT AAAGTCATGG TCAAAAAAGA AATAAAATGC AGTTAGGTTT   1668

GTGTTGCAGT TTTGATTCCT TGTATTGTTA CTTGTACTTT TGATCTTTTT CTTTTTTAAT   1728

GAAATTCTC TCTTTGTTTT GTGAAAAAAA AAAAAAAAAA GAGCTCCTGC AGAAGCTT   1786
```

FIG. 1F

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 1:

| Ala | Ile | Leu | Val | Thr | Gly | Ala | Thr | Gly | Ser | Leu | Ala | Lys |
|-----|-----|-----|-----|-----|-----|-----|-----|-----|-----|-----|-----|-----|
| 1   |     |     |     | 5   |     |     |     |     | 10  |     |     |     |

( 2 ) INFORMATION FOR SEQ ID NO: 2:

( i ) SEQUENCE CHARACTERISTICS:
        ( A ) LENGTH: 12 amino acids
        ( B ) TYPE: amino acid (D) TOPOLOGY: linear (ii) MOLECULE TYPE: peptide (xi) SEQUENCE DESCRIPTION: SEQ ID NO: 2:

```
Leu Gln Asn Glu Xaa Phe Gly Lys Glu Leu Phe Lys
1               5                   10
```

(2) INFORMATION FOR SEQ ID NO: 3:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 3:

```
Val Thr Val Val Pro Gly Asp Ile Thr Gly Glu Asp Leu
1               5                   10
```

(2) INFORMATION FOR SEQ ID NO: 4:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 4:

```
Leu Gly Leu Asp Ile Asn Val Glu Lys
1               5
```

(2) INFORMATION FOR SEQ ID NO: 5:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 5:

```
Thr Ile Asp Asn Val Pro Val Tyr Tyr Gly Lys
1               5                   10
```

(2) INFORMATION FOR SEQ ID NO: 6:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO: 6:

```
Tyr Val Glu Pro Val Thr Tyr His Val Gly Ser Ser Ala Ala Asn Pro
1               5                   10                  15
Met
```

(2) INFORMATION FOR SEQ ID NO: 7:

(i) SEQUENCE CHARACTERISTICS:
        (A) LENGTH: 10
        (B) TYPE: amino acid
        (D) TOPOLOGY: linear (ii) MOLECULE TYPE: peptide (xi) SEQUENCE DESCRIPTION: SEQ ID NO: 7:

Leu Ser Ala Leu Pro Glu Met Ala His Arg
1               5                   10

( 2 ) INFORMATION FOR SEQ ID NO: 8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 8 :

Leu Val Asp Ile Tyr Lys
1               5

( 2 ) INFORMATION FOR SEQ ID NO: 9:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 9:

Glu Gly Ile Val Glu Ala Asp Met Phe Tyr Phe Asp
1               5                   10

( 2 ) INFORMATION FOR SEQ ID NO: 10:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 10:

Ala Ile Asn Trp Glu Asp Tyr Phe Leu Lys Thr Xaa Phe Pro Gly Val
1               5                   10                  15

Val Glu Xaa Val Leu
                20

( 2 ) INFORMATION FOR SEQ ID NO: 11:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 11:

Ala Ile Leu Val Thr Gly Ala Thr Gly Ser Leu Ala Lys
1               5                   10

( 2 ) INFORMATION FOR SEQ ID NO: 12:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 12:

Leu Gly Leu Asp Ile Asn Val Glu Lys
1               5

(2) INFORMATION FOR SEQ ID NO: 13:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 13:

```
Thr Ile Asp Asn Val Pro Val Tyr Tyr Gly
 1               5                  10
```

(2) INFORMATION FOR SEQ ID NO: 14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 14:

```
Tyr Val Glu Pro Val Thr Tyr Xaa Val Gly Ser Ser Ala Ala Asn
 1               5                  10                   15
```

(2) INFORMATION FOR SEQ ID NO: 15:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 15:

```
Leu Val Asp Ile Tyr Lys Pro
 1               5
```

(2) INFORMATION FOR SEQ ID NO: 16:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO: 16:

```
Glu Gly Ile Val Glu Ala Asp Met Phe Tyr Phe
 1               5                  10
```

(2) INFORMATION FOR SEQ ID NO: 17:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 17:

```
Ala Ile Asn Trp Glu Asp Tyr Phe Leu
 1               5
```

(2) INFORMATION FOR SEQ ID NO: 18:

(i) SEQUENCE CHARACTERISTICS:
        (A) LENGTH: 11 amino acids
        (B) TYPE: amino acid
        (D) TOPOLOGY: linear (i i) MOLECULE TYPE: peptide (x i) SEQUENCE DESCRIPTION: SEQ ID NO: 18:

```
Thr His Phe Pro Gly Val Val Glu His Val Leu
 1               5                   10
```

(2) INFORMATION FOR SEQ ID NO: 19:

(i) SEQUENCE CHARACTERISTICS:
        (A) LENGTH: 1786 base pairs
        (B) TYPE: nucleic acid
        (C) STRANDEDNESS: double
        (D) TOPOLOGY: linear (i i) MOLECULE TYPE: cDNA to mRNA (x i) SEQUENCE DESCRIPTION: SEQ ID NO: 19:

```
AAATCCTCCA CTCATACACT CCACTTCTCT CTCTCTCTCT CTCTCTCTGA AACAATTTGA        60

GTAGCAAACT TAAAAGAAA ATG GAG GAA ATG GGA AGC ATT TTA GAG TTT CTT        112
                    Met Glu Glu Met Gly Ser Ile Leu Glu Phe Leu
                     1               5                   10

GAT AAC AAA GCC ATT TTG GTC ACT GGT GCT ACT GGC TCC TTA GCA AAA        160
Asp Asn Lys Ala Ile Leu Val Thr Gly Ala Thr Gly Ser Leu Ala Lys
             15                  20                  25

ATT TTT GTG GAG AAG GTA CTG AGG AGT CAA CCG AAT GTG AAG AAA CTC        208
Ile Phe Val Glu Lys Val Leu Arg Ser Gln Pro Asn Val Lys Lys Leu
         30                  35                  40

TAT CTT CTT TTG AGA GCA ACC GAT GAC GAG ACA GCT GCT CTA CGC TTG        256
Tyr Leu Leu Leu Arg Ala Thr Asp Asp Glu Thr Ala Ala Leu Arg Leu
     45                  50                  55

CAA AAT GAG GTT TTT GGA AAA GAG TTG TTC AAA GTT CTG AAA CAA AAT        304
Gln Asn Glu Val Phe Gly Lys Glu Leu Phe Lys Val Leu Lys Gln Asn
 60              65                  70                      75

TTA GGT GCA AAT TTC TAT TCC TTT GTA TCA GAA AAA GTG ACT GTA GTA        352
Leu Gly Ala Asn Phe Tyr Ser Phe Val Ser Glu Lys Val Thr Val Val
                 80                  85                  90

CCC GGT GAT ATT ACT GGT GAA GAC TTG TGT CTC AAA GAC GTC AAT TTG        400
Pro Gly Asp Ile Thr Gly Glu Asp Leu Cys Leu Lys Asp Val Asn Leu
             95                 100                 105

AAG GAA GAA ATG TGG AGG GAA ATC GAT GTT GTT GTC AAT CTA GCT GCT        448
Lys Glu Glu Met Trp Arg Glu Ile Asp Val Val Val Asn Leu Ala Ala
         110                 115                 120

ACA ATC AAC TTC ATT GAA AGG TAC GAC GTG TCT CTG CTT ATC AAC ACA        496
Thr Ile Asn Phe Ile Glu Arg Tyr Asp Val Ser Leu Leu Ile Asn Thr
     125                 130                 135

TAT GGA GCC AAG TAT GTT TTG GAC TTC GCG AAG AAG TGC AAC AAA TTA        544
Tyr Gly Ala Lys Tyr Val Leu Asp Phe Ala Lys Lys Cys Asn Lys Leu
140                 145                 150                 155

AAG ATA TTT GTT CAT GTA TCT ACT GCT TAT GTA TCT GGA GAG AAA AAT        592
Lys Ile Phe Val His Val Ser Thr Ala Tyr Val Ser Gly Glu Lys Asn
                 160                 165                 170

GGG TTA ATA CTG GAG AAG CCT TAT TAT ATG GGC GAG TCA CTT AAT GGA        640
Gly Leu Ile Leu Glu Lys Pro Tyr Tyr Met Gly Glu Ser Leu Asn Gly
             175                 180                 185

AGA TTA GGT CTG GAC ATT AAT GTA GAG AAG AAA CTT GTG GAG GCA AAA        688
Arg Leu Gly Leu Asp Ile Asn Val Glu Lys Lys Leu Val Glu Ala Lys
         190                 195                 200

ATC AAT GAA CTT CAA GCA GCG GGG GCA ACG GAA AAG TCC ATT AAA TCG        736
Ile Asn Glu Leu Gln Ala Ala Gly Ala Thr Glu Lys Ser Ile Lys Ser
     205                 210                 215

ACA ATG AAG GAC ATG GGC ATC GAG AGG GCA AGA CAC TGG GGA TGG CCA        784
Thr Met Lys Asp Met Gly Ile Glu Arg Ala Arg His Trp Gly Trp Pro
```

|     | 220 |     |     |     | 225 |     |     |     | 230 |     |     |     | 235 |     |     |
| --- | --- | --- | --- | --- | --- | --- | --- | --- | --- | --- | --- | --- | --- | --- | --- |
| AAT | GTG | TAT | GTA | TTC | ACC | AAG | GCA | TTA | GGG | GAG | ATG | CTT | TTG | ATG | CAA | 832 |
| Asn | Val | Tyr | Val | Phe 240 | Thr | Lys | Ala | Leu | Gly 245 | Glu | Met | Leu | Leu | Met 250 | Gln |
| TAC | AAA | GGG | GAC | ATT | CCG | CTT | ACT | ATT | ATT | CGT | CCC | ACC | ATC | ATC | ACC | 880 |
| Tyr | Lys | Gly | Asp 255 | Ile | Pro | Leu | Thr | Ile 260 | Ile | Arg | Pro | Thr | Ile 265 | Ile | Thr |
| AGC | ACT | TTT | AAA | GAG | CCC | TTT | CCT | GGT | TGG | GTT | GAA | GGT | GTC | AGG | ACC | 928 |
| Ser | Thr | Phe 270 | Lys | Glu | Pro | Phe 275 | Pro | Gly | Trp | Val | Glu | Gly 280 | Val | Arg | Thr |
| ATC | GAT | AAT | GTA | CCT | GTA | TAT | TAT | GGT | AAA | GGG | AGA | TTG | AGG | TGT | ATG | 976 |
| Ile | Asp 285 | Asn | Val | Pro | Val | Tyr 290 | Tyr | Gly | Lys | Gly | Arg 295 | Leu | Arg | Cys | Met |
| CTT | TGC | GGA | CCC | AGC | ACA | ATA | ATT | GAC | CTG | ATA | CCG | GCA | GAT | ATG | GTC | 1024 |
| Leu 300 | Cys | Gly | Pro | Ser | Thr 305 | Ile | Ile | Asp | Leu | Ile 310 | Pro | Ala | Asp | Met | Val 315 |
| GTG | AAT | GCA | ACG | ATA | GTA | GCC | ATG | GTG | GCG | CAC | GCA | AAC | CAA | AGA | TAC | 1072 |
| Val | Asn | Ala | Thr | Ile 320 | Val | Ala | Met | Val | Ala 325 | His | Ala | Asn | Gln | Arg 330 | Tyr |
| GTA | GAG | CCG | GTG | ACA | TAC | CAT | GTG | GGA | TCT | TCA | GCG | GCG | AAT | CCA | ATG | 1120 |
| Val | Glu | Pro | Val 335 | Thr | Tyr | His | Val | Gly 340 | Ser | Ser | Ala | Ala | Asn 345 | Pro | Met |
| AAA | CTG | AGT | GCA | TTA | CCA | GAG | ATG | GCA | CAC | CGT | TAC | TTC | ACC | AAG | AAT | 1168 |
| Lys | Leu | Ser 350 | Ala | Leu | Pro | Glu | Met 355 | Ala | His | Arg | Tyr | Phe 360 | Thr | Lys | Asn |
| CCA | TGG | ATC | AAC | CCG | GAT | CGC | AAC | CCA | GTA | CAT | GTG | GGT | CGG | GCT | ATG | 1216 |
| Pro | Trp 365 | Ile | Asn | Pro | Asp | Arg 370 | Asn | Pro | Val | His | Val 375 | Gly | Arg | Ala | Met |
| GTC | TTC | TCC | TCC | TTC | TCC | ACC | TTC | CAC | CTT | TAT | CTC | ACC | CTT | AAT | TTC | 1264 |
| Val 380 | Phe | Ser | Ser | Phe | Ser 385 | Thr | Phe | His | Leu | Tyr 390 | Leu | Thr | Leu | Asn | Phe 395 |
| CTC | CTT | CCT | TTG | AAG | GTA | CTG | GAG | ATA | GCA | AAT | ACA | ATA | TTC | TGC | CAA | 1312 |
| Leu | Leu | Pro | Leu | Lys 400 | Val | Leu | Glu | Ile | Ala 405 | Asn | Thr | Ile | Phe | Cys 410 | Gln |
| TGG | TTC | AAG | GGT | AAG | TAC | ATG | GAT | CTT | AAA | AGG | AAG | ACG | AGG | TTG | TTG | 1360 |
| Trp | Phe | Lys | Gly 415 | Lys | Tyr | Met | Asp | Leu 420 | Lys | Arg | Lys | Thr | Arg 425 | Leu | Leu |
| TTG | CGT | TTA | GTA | GAC | ATT | TAT | AAA | CCC | TAC | CTC | TTC | TTC | CAA | GGC | ATC | 1408 |
| Leu | Arg | Leu 430 | Val | Asp | Ile | Tyr | Lys 435 | Pro | Tyr | Leu | Phe | Phe 440 | Gln | Gly | Ile |
| TTT | GAT | GAC | ATG | AAC | ACT | GAG | AAG | TTG | CGG | ATT | GCT | GCA | AAA | GAA | AGC | 1456 |
| Phe | Asp | Asp 445 | Met | Asn | Thr | Glu | Lys 450 | Leu | Arg | Ile | Ala | Ala 455 | Lys | Glu | Ser |
| ATA | GTT | GAA | GCT | GAT | ATG | TTT | TAC | TTT | GAT | CCC | AGG | GCA | ATT | AAC | TGG | 1504 |
| Ile 460 | Val | Glu | Ala | Asp | Met 465 | Phe | Tyr | Phe | Asp | Pro 470 | Arg | Ala | Ile | Asn | Trp 475 |
| GAA | GAT | TAC | TTC | TTG | AAA | ACT | CAT | TTC | CCA | GGN | GTC | GTA | GAG | CAC | GTT | 1552 |
| Glu | Asp | Tyr | Phe | Leu 480 | Lys | Thr | His | Phe | Pro 485 | Gly | Val | Val | Glu | His 490 | Val |

```
CTT AAC TAAAAGTTAC GGTACGAAAA TGAGAAGATT GGAATGCATG CACCGAAAGN       1608
Leu Asn
NCAACATAAA AGACGTGGTT AAAGTCATGG TCAAAAAGA AATAAATGC AGTTAGGTTT      1668
GTGTTGCAGT TTTGATTCCT TGTATTGTTA CTTGTACTTT TGATCTTTTT CTTTTTAAT     1728
GAAATTTCTC TCTTTGTTTT GTGAAAAAAA AAAAAAAAA GAGCTCCTGC AGAAGCTT       1786
```

FATTY ACYL REDUCTASES

This application is a continuation-in-part of PCT/US92/01364 filed Feb. 21, 1992, and a continuation-in-part of U.S. Ser. No. 07/796,256 filed Nov. 20, 1991, now abandoned, and a continuation-in-part of U.S. Ser. No. 07/767,251 filed Sep. 27, 1991 and a continuation-in-part of U.S. Ser. No. 07/659,975 filed Feb. 22, 1991, now abandoned.

TECHNICAL FIELD

The present invention is directed to plant enzymes, methods to purify, and obtain such enzymes, amino acid and nucleic acid sequences related thereto, and methods of use for such compositions.

INTRODUCTION

Background

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bands. As the carbon chain of fatty acyl molecules always contains an even number of carbons, the formula "$C_{2x}$" may also be used to represent carbon chain length.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

Many plants have been studied which store lipid as triacylglycerols composed primarily of long chain (having 16 or 18 carbons) fatty acyl groups. Very long chain (having 20-24 carbons) monounsaturated fatty acyl groups are formed by an acyl-CoA elongation pathway from C18:1 and are found in many plant seeds, notably members of the Crucifereae family. The desert shrub, *Simmondsia chinensis*, better known as jojoba, is unique among higher plants (seed-bearing plants) in its ability to produce and store large amounts of liquid wax as the major component of its seed storage lipid. These simple wax compounds are oxygen esters of very long-chain monoenoic fatty acyl groups and alcohols.

Other types of waxes are formed by some plant species. The synthesis of plant epidermal, or cuticular wax, as well as wax synthesis by bacteria, such as Acinetobacter (Fixter et al. (1986) *J. Gen. Microbiol.* 132:3147-3157) and *Micrococcus* (Lloyd (1987) *Microbios* 52:29-37), and by the unicellular green algae, Euglena, are well known. However, the composition and biosynthetic pathway of these waxes differs from the jojoba seed wax.

In the formation of Euglena storage wax for instance, it has been demonstrated that the alcohol portion is formed by an NADH-dependent reduction of a fatty acyl compound catalyzed by a fatty acyl-CoA reductase. In jojoba seeds, the reaction is NADPH-dependent. It has been postulated that the reduction of a very long chain fatty acyl-CoA to the corresponding alcohol is dependent upon a single enzyme whose activity has been observed in crude extracts from developing jojoba seeds (Pollard et al. (1979) *Lipids* 14:651–662; Wu et al. (1981) *Lipids* 16:897–902). Also, by comparison, for the formation of plant cuticular waxes, a two step process has been reported (Kolattukudy (1980) in *The Biochemistry of Plants* (Stumpf, P. K. and Conn, E. E., eds.) Vol. 4, p. 571–645). The fatty acyl-CoA is converted to a free aldehyde by the action of an NADH-dependent reductase and the alcohol is subsequently formed by the action of an NADPH-dependent fatty aldehyde reductase.

Further characterization of the enzymes responsible for formation of wax esters in plants has been hindered by the lack of protocols which result in the identification of polypeptides associated with the enyzmatic activity. It is desirable, therefore, for further study of plant fatty acyl reductase proteins to devise a purification protocol whereby the reductase polypeptide(s) can be identified. By establishing these methods, sufficient amounts of plant fatty acyl reductase protein may be obtained, the amino acid sequence of the protein may be determined and/or antibodies specific for the fatty acyl reductase may be obtained. The resulting amino acid sequences may be useful in polymerase chain reaction (PCR) techniques or for screening cDNA or genomic libraries. Alternatively, antibodies may be used for screening expression libraries to identify clones expressing fatty acyl reductase protein. Clones obtained in this manner can be analyzed so that the nucleic acid sequences corresponding to plant fatty acyl reductase are identified.

Relevant Literature

Cell-free homogenates from developing jojoba embryos were reported to have NADPH-dependent fatty acyl-CoA reductase activity. The activity was associated with a floating wax pad which formed upon differential centrifugation (Pollard et al. (1979) supra; Wu et al. (1981) supra).

Conservation of functional residues in known dinucleotide binding folds of several reductase proteins is presented by Karplus et al. (*Science* (1991) 251:60–66).

Solubilization of a multienzyme complex from *Euglena gracilis* having fatty acyl-CoA reductase activity is reported by Wildner and Hallick (Abstract from *The Southwest Consortium Fifth Annual Meeting*, Apr. 22-24, 1990, Las Cruces, N. Mex.).

3000-fold purification of jojoba reductase protein is reported by Pushnik et al. (Abstract from *The Southwest Consortium Fourth Annual Meeting*, Feb. 7, 1989, Riverside, Calif.).

BRIEF DESCRIPTION OF THE FIGURES

FIG. 1. Nucleic acid sequence and translated amino acid sequence of a jojoba fatty acyl reductase is provided (SEQ ID NO: 19).

SUMMARY OF THE INVENTION

By this invention, a partially purified fatty acyl reductase protein is provided, wherein said protein is active in the formation of a fatty alcohol from a fatty acyl substrate. The reductase of this invention may be active with a variety of fatty acyl substrates, including acyl-CoAs and acyl-ACPs. The carbon chain length of these substrates may vary, although a given reductase may show preference for a specific chain length acyl substrate or may be active with acyl substrates having a wide range with respect to carbon chain length.

In general, the reductase of this invention has activity towards at least those acyl substrates having a chain length of from 16 to 24 carbons, which carbon chain length may be represented by the formula "$C_{2x}$", where "x" is a number from 8 to 12, although other acyl substrates may be tested and further activities discovered. In addition, having obtained the reductase protein of this invention, further manipulations are now possible as described in further detail below. These manipulations may lead to production or discovery of other related reductases.

Thus, in a first aspect, this invention relates to protein preparations demonstrating fatty acyl reductase enzymatic activity, and is exemplified by a seed-plant protein preparation. Such a preparation is produced by fractionation of jojoba embryos to produce a microsomal membrane preparation, solubilization of the reductase protein from this membrane preparation and further purification by chromatographic procedures. The jojoba reductase is shown to prefer very long chain acyl-CoA substrates, although activity with other acyl substrates is also observed, and is confirmed to be NADPH-dependent.

By these procedures, a partially purified reductase preparation is obtained which contains two prominent polypeptides which migrate as a doublet band on polyacrylamide gels, and which have apparent molecular masses of approximately 54 and 52 kD. Thus, methods of obtaining acyl reductase proteins through purification from seed-plant sources are provided, as well as methods to obtain amino acid sequences of these reductase proteins.

In a different aspect of this invention, nucleic acid sequences associated with a reductase of this invention are considered. Methods are described whereby these sequences may be identified and obtained from the amino acid sequences of the reductase proteins of this invention. Uses of the structural gene sequences for isolation of other reductase sequences, as well as in recombinant constructs for transcription of reductase nucleic acid sequences and/or expression of reductase proteins in host cells are described. Uses of other nucleic acid sequences associated with reductase protein are also considered, such as the use of 5' and 3' noncoding regions.

In yet a different aspect of this invention, cells containing the recombinant constructs of this invention are considered. In particulars cells which contain the preferred substrates of a jojoba reductase, such as those cells in embryos of Brassica plants, are considered.

In addition, cells containing the reductase protein of this invention as the result of expression from the recombinant constructs of this invention are considered, and a method of producing a reductase in a host cell is provided. Accordingly, a reductase protein that is recovered as the result of expression of that protein in a host cell is also considered in this invention. Further, it may be recognized that the reductases of this invention find application in the production of fatty alcohols in such host cells.

DETAILED DESCRIPTION OF THE INVENTION

A fatty acyl reductase of this invention includes any sequence of amino acids, such as protein, polypeptide or peptide fragment, which is active in catalyzing the reduction of a fatty acyl group to the corresponding alcohol. By fatty acyl group is intended any fatty acyl group, covalently bound to a carrier, such as ACP or coenzyme A.

Other enzymes may or may not be required for the reduction of the fatty acyl group to the alcohol, as this enzymatic reaction involves a 4 electron reduction which may be carried out in two steps. In the first step, the acyl group may be converted to an aldehyde, which would then be reduced to the corresponding alcohol. Thus, the reductase of this invention may be active through the entire 4 electron reduction, from acyl to alcohol, or may catalyze the reduction to the aldehyde, which is then further reduced to the alcohol by a second enzyme. Evidence obtained thus far indicates a single enzyme carries out the complete reduction of acyl CoA to alcohol. The fatty acyl reductase of this invention is also referred to hereafter as "acyl reductase" or "reductase".

Thus, this invention relates to seed-plant fatty acyl reductases which convert fatty acyl groups to alcohols. More particularly, this invention relates to NADPH-dependent reductases. In addition, it is noted that a plant fatty acyl reductase of this invention may have activity towards both fatty acyl-CoA or fatty acyl-ACP molecules, and the activity observed may depend upon the substrate available. However, preferential activity toward very long chain acyl-CoA substrates is desired for manipulation of the fatty acid synthetase (FAS) acyl-CoA elongation pathway.

By this invention, it has been determined that the seed-plant fatty acyl reductase protein is an integral membrane protein. In general, membrane associated proteins are difficult to purify as they tend to lose enzymatic activity when they are solubilized, i.e. separated from the membrane environment in which they normally function. However, obtaining a solubilized seed-plant fatty acyl reductase which still retains its enzymatic activity can permit various uses which are not possible with a membrane-bound protein.

For example, once a purified or partially purified acyl reductase protein is obtained, it may be immobilized and used in a reactor system to prepare fatty alcohols in the presence of a reduced pyridine nucleotide regenerating system. Further, study of the reductase protein may lead to site mutagenesis studies to further characterize and improve its catalytic properties or to alter its acyl substrate specificity. A reductase with altered substrate specificity may find application in conjunction with other FAS enzymes. For example, a medium chain (C12–C14preferring plant thioesterase (see copending U.S. patent application Ser. No. 07/662,007), and an appropriate acyl transferase may be used in conjunction with an altered reductase to produce medium-chain alcohols, which may then be esterified to fatty acids to yield esters.

One significant factor to be considered when working with membrane bound proteins is the extent of the association of the protein with the membrane. Both peripheral and integral membrane proteins are known. Peripheral proteins are typically somewhat hydrophilic in nature, only loosely associated with the membranes and easily solubilized. Integral proteins, on the contrary, have highly hydrophobic regions embedded in the lipid membrane and often must be associated with lipids if they are to retain enzymatic activity.

Techniques that have been used to solubilize integral membrane proteins include addition of detergents or organic solvents to a preparation of a suitable membrane fraction. Further conventional purification techniques, such as precipitation, ion-exchange, gel-filtration and affinity chromatography may then be utilized, assuming the desired protein still retains functional activity that can be measured using a specific enzymatic assay.

Typically, as a first step towards obtaining a solubilized protein preparation a microsomal membrane preparation of seed-plant tissue which comprises acyl reductase activity is desired. Standard microsomal membrane preparations utilize differential centrifugation of a cell-free homogenate (CFH) to yield a membrane fraction which is free of whole cells, nuclei and soluble protein. (See, for example Mooré et al. (1987) *Biological Membranes: A Practical Approach*, pp. 37–72, eds. Finalay and Evans.) With oilseed, initial centrifugation steps typically yield a pellet, supernatant and a floating fat pad, and microsomal members may then be recovered by further centrifugation of the supernatant.

A protocol has been described in co-pending U.S. Ser. No. 07/659,975, filed Feb. 22, 1991, whereby a membrane fraction containing active acyl reductase protein was obtained with good recovery of reductase activity relative to that in the CFH. A critical step in this process was the removal of the seed coat from the jojoba embryos as the coats are found to contain a factor(s) that interferes with enzymological measurements. The method employs a high salt solution during the initial portion of the protocol, the steps of which are also described below and in more detail in the examples which follow.

A powder is produced from a jojoba embryo sample, and a homogenate is prepared by homogenizing the powder in a high salt (3 M NaCl) sucrose (0.3 M) solution at a ratio of 80 ml of solution per 20 gm embryos. The homogenate is then filtered and centrifuged at 100,000×g for approximately one hour, wherein a pellet, supernatant and a floating fat pad are obtained. The fat pad is removed and the supernatant is collected and dialyzed against a 1 M NaCl solution which also contains 100 mM HEPES (pH 7.5), 2 mM DTT and 0.5 mM EDTA. The dialyzate is then centrifuged at 100,000×g, or more preferably at 200,000×g for approximately one hour, wherein a pellet, DP2, is obtained which comprises microsomal membranes having acyl-CoA reductase activity.

Further characterization of the acyl reductase activity in the microsomal membrane preparation and during further purification procedures may be facilitated by developing an optimized specific assay for the acyl reductase. For example, with jojoba an assay is employed which utilizes very long chain acyl-CoA molecules as substrates and which is conducted under high salt (0.2 M to 0.5 M NaCl) conditions, high salt having been found to significantly increase the detectable acyl-CoA reductase activity. This assay is described in detail in Example 1.

Another critical stage for further enzyme characterization and purification is that of obtaining solubilized reductase protein that is separated from its native lipid bilayer membrane environment, but retains substantial amounts of measurable reductase enzymatic activity. The removal of integral membrane proteins from the lipid bilayer is typically accomplished using amphiphilic detergents in aqueous solution, although organic solvents have also been used in a few cases. Many different detergents are available, both ionic and nonionic, which vary in their dissociating effects, critical micelle concentration (CMC), effect on enzymatic activity and further purification, and ease of removability from the solution. Many different detergents and methods of solubilization of membrane proteins are known to those skilled in the art, and are also reviewed by Neugebauer (*Methods Enzymol.* (1990) 182:239–253) and Hjelmiland (*Methods Enzymol.* (1990) 182:253–264).

Often, detergents which are used to solubilize membrane proteins are found to inhibit the enzymatic activity of a desired protein. Several detergents were tested for solubilization of jojoba acyl reductase, representing a wide range of characteristics, and all were found to be inhibitory. However, as apparent detergent inhibition of reductase activity may be due to some effect other than irreversible inhibition of the enzyme, the reversibility of inhibition by CHAPS was examined.

Although strong inhibition by the detergent CHAPS (3-[(3-cholamidopropyl)-dimethyl-ammonio]-1-propanesulfonate) at concentrations above the CMC was seen, it was found that if the enzyme was exposed to CHAPS on ice, and then returned to a CHAPS concentration at or below the CMC value, complete recovery of reductase activity was obtained. Thus, reductase is not irreversibly inhibited by the detergent CHAPS. A protocol for solubilizing jojoba acyl reductase activity utilizing the detergent CHAPS has been devised which yields approximately 85% of the reductase activity from the microsomal membrane preparation. This method is discussed in detail in Example 2. Similarly, studies of reversibility of apparent reductase inhibition by other detergents may be conducted to identify other useful detergents for solubilization of acyl reductase activity for jojoba or other candidate reductases.

Having obtained the solubilized acyl reductase protein, it can be seen that further experiments to characterize the enzyme as to substrate specificity, cofactor requirements and possible activity inhibiting agents may now be conducted. For example, it has been found that the jojoba acyl reductase of this invention has a broad range of substrates, including ACP and CoA substrates. For example, activity towards acyl-ACP substrates having at least 16 carbons is observed, as well as activity towards acyl-CoA substrates having at least 18 carbons. A preferred activity toward [C15]-15-tetracosenoyl-CoA (C24:1) is observed.

Protein preparations may be further enriched for a candidate plant acyl reductase protein, for example by chromatography over an immobilized reactive dye. Many such reactive dye matrices are known, including the Cibacron Blue F3GA (Blue A) used in this invention. By this invention it is demonstrated that jojoba acyl reductase activity binds to such a column when loaded in a buffer containing approximately 0.2 M NaCl, and more preferred 0.5 M NaCl, or more preferred 0.4 M NaCl, while greater than approximately 85% of other protein passes through or is removed in subsequent washes. Further, it is demonstrated that jojoba acyl activity can be recovered by elution from the Blue A column in a buffer containing approximately 1.0 M NaCl.

The acyl reductase activity is further purified by applying the enriched protein preparation from the Blue A column to a column packed with a size exclusion matrix also sometimes called a gel filtration column. The size exclusion column also provides an estimate of the size of the native reductase enzyme. In particulars a narrow range sizing column matrix, such as Ultragel AcA54 or Sephacryl S100, is useful in obtaining further purified jojoba acyl reductase fractions. Of special interest are methods and buffers which may be utilized to obtain recovery, in one main peak, of greater than approximately 40-60% of the reductase activity that is loaded to size exclusion a column or its equivalent.

Application of the reductase activity from a size exclusion column to an affinity column results in further purification of the reductase protein. For example, active fractions may be applied to a palmitoyl CoA agarose column in approximately 0.1 M NaCl. Approximately 70% of the reductase activity may then be eluted with a buffer having 15 mM NADPH, a cofactor of the reductase enzyme from jojoba.

Throughout the purification the fractions comprising acyl reductase activity of this invention may be subjected to further techniques, such as SDS polyacrylamide gel electrophoresis and subsequent staining. In this manner, the prominent polypeptide bands in these fractions having reductase activity can be identified. For example, in a partially purified jojoba reductase preparation from a palmitoyl CoA agarose columns two bands representing polypeptides of approximately 53 kD, more particularly polypeptides having a 54 and 52 kD apparent molecular mass are identified which constitute greater than 95% of the protein in the preparation. Further SDS-PAGE analysis using different markers indicates that the apparent molecular mass of these reductase proteins may be more accurately defined as 54 and 56 kD, or approximately 55 kD.

As the apparent size of the native reductase enzyme ms approximately 49 kD, as demonstrated by size exclusion chromatography herein, these bands do not likely represent two different subunits of one reductase enzyme. Rather, reductase activity is associated with either one or both of these polypeptides. Tests, including anion exchange, dye columns, hexanoyl-CoA affinity columns, gel filtration, heparin columns and thiol interactive chromatography, have failed to separate these polypeptides from reductase activity.

As the jojoba seeds used in this purification are collected from a diverse population of jojoba plants, these polypeptides may represent closely related variants of the same enzyme, i.e. isozymes. Alternatively, the smaller polypeptide band may represent a breakdown product of the larger band which occurs during purification. Western analysis, tryptic digestion and amino acid sequence analysis of the two polypeptides, as described herein, may be used to further characterize these protein bands.

Furthermore, it is recognized that the methods developed for purification of the jojoba reductase may now be applied to purification of similar membrane associated acyl-CoA reductases from other organisms. In this manner, a variety of reductases having a range of substrate preferences or specificities may be obtained. Other desirable sources of such reductases include Acinetobacter species, Micrococcus and green algae (Euglena).

Recovery of substantially purified reductase protein can now be accomplished using a variety of methods. For example, polyacrylamide gels may be run and the proteins transferred to a membrane support, such as nitrocellulose or polyvinylidenedifluoride (PVDF). The sections of these membranes which contain the identified proteins may then be obtained such that the identified proteins are substantially free of other proteins. Using techniques known in the art and also described in the following examples, the proteins may be removed from the membranes and further manipulated such that their amino acid sequences are determined.

For example, amino acid sequence can be determined by sequencing N-terminal amino acid regions from whole protein or by preparing fragments of the desired protein by digestion with the chemical cyanogen bromide, or alternatively by enzymatic cleavage using proteases. Examples of proteases which may be useful include endoproteinase lysC, gluC, AspN and trypsin. The fragments obtained in this manner may then be purified and sequenced in accordance with methods familiar to those skilled in the art.

Further characterization of the 54 and 52 kD candidate polypeptides may be useful, for example, expression of the respective proteins in *E. coli* and subsequent verification of reductase activity. Other testing may include immunological assays, whereby antibodies specific for the candidate protein are prepared and found to inhibit reductase activity in protein preparations.

Moreover, it is desirable to isolate nucleic acid sequences from amino acid sequences determined for the proteins associated with acyl reductase activity, both to confirm the identity of an acyl reductase protein and to provide for transcription of the sequences and/or expression of the protein in host cells, either prokaryotic or eukaryotic. When expressed in *E. coli* cells, the jojoba reductase nucleic acid sequences result in production of reductase activity, which is not present in control cells, and the formation of fatty alcohols. In particulars long chain 16:0 and 18:1 fatty alcohols are detected.

It is also desirable to express reductase proteins in plant cells in order to provide this reductase activity to plants not known to have such activity, or to affect the amount or specificity of reductase activity in plants which have such reductase activity. Electroporation or bombardment of plant tissue for transient expression may be useful for this purpose. Ultimately, stable expression of reductase protein in a plant, such as a member of the Brassica genus, which produces substrates recognized by this enzyme, is desired. In this manner, the acyl alcohol products, which have uses in pharmaceuticals, cosmetics, detergents, plastics, and lube oils may be obtained. As described herein, expression of the jojoba reductase in transgenic Arabidopsis plants results in the production of 20:1 alcohol in the seeds of these plants.

In some instances, for example with alternative sources of reductase, various manipulations may be necessary for expression of reductase activity in cells. For example, low level expression using a weak promoter may be desirable in a prokaryote, such as *E. coli*, to avoid possible disruptions of cell membranes from overexpression of these membrane proteins. Alternatively, leader peptides responsible for membrane insertion may be identified, and constructs prepared which contain only the mature reductase encoding sequence. If reductase activity is not detectable in *E. coli*, for example if the protein is not inserted into the membrane bilayer, the presence of the reductase protein in *E. coli* cells may be confirmed by other means, such as using antibody preparations.

The reductase nucleic acids of this invention may be genomic or cDNA and may be isolated from cDNA or genomic libraries or directly from isolated plant DNA. Methods of isolation of gene sequences once a protein is isolated and/or amino acid sequence of the protein is obtained are known those skilled in the art.

For example, antibodies may be raised to the isolated protein and used to screen expression libraries, thus identifying clones which produce the plant acyl reductase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

Acyl reductase nucleic acid sequences of this invention include those corresponding to the jojoba acyl-CoA reductase protein, as well as sequences obtainable from the jojoba protein or nucleic acid sequences. By "corresponding" is meant nucleic acid sequences, either DNA or RNA, including those which encode jojoba acyl reductase protein or a portion thereof, regulatory sequences found 5' or 3' to said encoding sequences which direct the transcription or transcription and translation (expression) of the reductase in jojoba embryos, intron sequences not present in the cDNA, as well as sequences encoding any leader or signal peptide of a precursor reductase protein that may be required for insertion into the endoplasmic reticulum membrane, but is not found in the mature, or processed, acyl reductase enzyme.

By sequences "obtainable" from the jojoba sequence or protein, is intended any nucleic acid sequences associated with a desired fatty acid reductase protein that may be synthesized from the jojoba acyl reductase amino acid sequence, or alternatively identified in a different organism and isolated using jojoba reductase nucleic acid sequences or antibodies prepared against the jojoba reductase protein as probes. In this manner, it can be seen that sequences of other acyl reductases that are isolated from a desired organism using the jojoba sequences, either by nucleic acid hybridization or antigenic methods, may similarly be used to isolate still other acyl reductases. Such reductases which are derived through seed-plant reductases isolated via jojoba reductase are likewise considered "obtainable" herein.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual*, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding acyl reductase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding an acyl reductase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba acyl reductase can be prepared by injecting rabbits or mice with the purified protein, such methods of preparing antibodies being well known to those in the art. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba reductase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some available systems have been described by Oberfelder (*Focus* (1989) BRL/Life Technologies, Inc. 11:1-5). When cross-reactivity is observed, genes encoding the related proteins are isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related acyl reductase protein. Other seed-plant fatty acyl reductases may be obtained through the use of these reductases in the same manner as the jojoba reductase was used.

It will be recognized by one of ordinary skill in the art that acyl reductase nucleic acid sequences of this invention may be modified using standard techniques of site specific mutation or PCR, or modification of the sequence may be accomplished in producing a synthetic nucleic acid sequence. These modified sequences are also considered acyl reductase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an acyl reductase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the reductase protein) may be synthesized using codons preferred by a selected host. Host-preferred codons may be determined, for example, from the codons used most frequently in the proteins expressed in a desired host species.

The nucleic acid sequences associated with acyl reductase proteins will find many uses. For example, recombinant constructs can be prepared which can be used as probes or will provide for expression of the acyl reductase protein in host cells. Depending upon the intended use, the constructs may contain the sequence which encodes the entire reductase, or a portion thereof. For example, critical regions of the reductase, such as an active site may be identified. Further constructs containing only a portion of the reductase sequence which encodes the amino acids necessary for a desired reductase activity may thus be prepared.

Expression in host cells which contain preferred substrates of the acyl reductase protein, allows for production of fatty acyl alcohols from the corresponding fatty acyl substrates. Useful systems for expression of the reductase protein include prokaryotic cells, such as *E. coli*, yeast cells, and plant cells, both vascular and nonvascular plant cells being desired hosts. In this manner, the reductase protein may be produced. In addition, site-specific mutagenesis of encoding sequences may be used to study the effects of specific mutations on reactive properties of the reductase protein.

Additionally, antisense constructs may be prepared which provide for transcription of a complementary sequence of an acyl reductase encoding sequence or fragment thereof. In this manner, the amount of the reductase protein produced in a target host organism may be reduced.

The DNA sequence encoding an acyl reductase of this invention may be combined with foreign DNA sequences in a variety of ways. By "foreign" DNA sequences is meant any DNA sequence which is not naturally found joined to the reductase, including combinations of DNA sequences from the same organism which are not naturally found joined together. For example, it may be desirable to join sequences encoding a transit peptide to reductase sequences of this invention. In this manner, the reductase may be targeted to a chloroplast where fatty acyl substrates, particularly fatty acyl-ACPs are available.

The DNA sequence encoding an acyl reductase of this invention may be employed in conjunction with all or part of the gene sequences normally associated with the reductase. In its component parts, a DNA sequence encoding reductase is combined in a recombinant construct having, in the 5' to 3' direction of transcription, a transcription initiation control region capable of promoting transcription and translation in a host cell, the nucleic acid sequence encoding reductase and a transcription termination region.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the recombinant constructs will involve regulatory regions functional in plants which provide for production of acyl reductase. The open reading frame, coding for the plant reductase or functional fragment thereof will be joined at its 5' end to a transcription initiation regulatory region. Translational initiation regions may also be desirable and may be provided from the 5' non-coding region of the reductase cDNA sequence or from the translational initiation region naturally associated with the transcription initiation region of the construct. Generally, the combination of transcriptional and translational regulatory regions is referred to as a promoter. Numerous promoter regions are available which provide for a wide variety of constitutive or regulatable, e.g., inducible, expression of structural genes in plants.

Among sequences known to be useful in providing for constitutive gene expression in plants are regulatory regions associated with Agrobacterium genes, such as those for nopaline synthase (Nos), mannopine synthase (Mas), or octopine synthase (Ocs), as well as regions coding for expression of vital genes, such as the 35S and 19S regions of cauliflower mosaic virus (CaMV). The term constitutive as used herein does not necessarily indicate that a gene ms expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

In embodiments wherein the expression of the acyl reductase protein is desired in a plant host, the use of all or part of the complete plant acyl reductase gene may be desired, namely the 5' upstream non-coding regions (promoter) together with the structural gene sequence and 3' downstream non-coding regions may be employed. For example, as the jojoba reductase cDNA is now known, the promoter associated with the reductase structural gene may be obtained for jojoba genomic DNA using PCR of hybridization techniques. If a different promoter is desired, such as a promoter native to the plant host of interest or a modified promoter, i.e., having transcription initiation regions derived from one gene source and translation initiation regions derived from a different gene source, or enhanced promoters, such as double 35S CaMV promoters, the sequences may be joined together using standard techniques.

For applications when 5' upstream non-coding regions are obtained from other genes regulated during seed maturation, Chose preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/742,834, filed Aug. 8, 1991), and U.S. Ser. No. 07/494,722 filed on or about Mar. 16, 1990 having a title "Novel Sequences Preferentially Expressed In Early Seed Development and Methods Related Thereto", all of which copending applications are incorporated herein by reference. Transcription initiation regions which are preferentially expressed in seed tissue are considered desirable for fatty alcohol production in order to minimize any disruptive or adverse effects of the gene product in other plant parts.

Regulatory transcription termination regions may be provided in recombinant constructs of this invention as well. Transcription termination regions may be provided by the DNA sequence encoding the plant acyl reductase or a convenient transcription termination region derived from a different gene source, especially the transcription termination region which is naturally associated with the transcription initiation region. The transcript termination region will typically contain at least about 0.5 kb, preferably about 1–3 kb of sequence 3' to the structural gene from which the termination region is derived.

Plant expression constructs having a plant acyl reductase as the DNA sequence of interest for expression thereof may be employed with a wide variety of plant life, particularly, plant life which produce very long chain fatty acyl-CoA molecules, such as Brassica, and in particular high erucic acid varieties of rapeseed. Other plants of interest produce desirable substrates, such as medium or long chain fatty acyl molecules, and include but are not limited to rapeseed (Canola varieties), Arabidopsis, sunflower, safflower, cotton, Cuphea, soybean, peanut, coconut and oil palms, and corn. Depending on the method for introducing the DNA expression constructs into the host cell, other DNA sequences may be required. Importantly, this invention is applicable to dicotyledyons and monocotyledons species alike and will be readily applicable to new and/or improved transformation and regeneration techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite mating or binary vector methods of Agrobacterium mediated transformation. Other sequences useful in providing for transfer of nucleic acid sequences to host plane cells may be derived from plant pathogenic viruses or plant transposable elements. In addition, techniques of microinjection, DNA particle bombardment, electroporation have been developed which allow for the transformation of various monocot and dicot plant species.

In developing the recombinant construct, the various components of the construct or fragments thereof will normally be inserted into a convenient cloning vector which is capable of replication in a bacterial host, e.g., E. coli. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the different hose species into which the expression constructs are introduced, one or more markers may be employed for selection or detection of transformed tissues, where different conditions for selection are used for the different hosts.

When Agrobacterium is utilized for plant transformation, it may be desirable to have the nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri-containing the T-DNA for recombination may be armed (capable of causing gall formation), or disarmed (incapable of causing gall formation), the latter being permissible so long as a functional complement of the vir genes, which encode transacting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region(s) will be inserted into a broad host range vector capable of replication in *E. coli* and Agrobacterium, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in Agrobacterium. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells.

For transformation of Brassica cells, for example, Agrobacterium transformation methods may be used. One such method is described by Radke et al. (*Theor. Appl. Genet.* (1988) 75:685–694).

The invention now being generally described, it will be more readily understood by reference to the following examples, which are included for purposes of illustration only and are not intended to limit the invention unless so stated.

EXAMPLES

Example 1-Acyl-CoA Reductase Assays

Methods to assay for acyl-CoA reductase activity in microsomal membrane preparations or solubilized protein preparations are described.

A. Radiolabeled Material

Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C] cyanide with the corresponding alkyl mesylate, followed by the base hydrolysis of the alkyl nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10 Ci/mole. Other [1-$^{14}$C] acyl-CoAs, such as [1-$^{14}$C]tetracasenoyl-CoA, were purchased from Amersham (Arlington Heights, Ill.). [1-$^{14}$C]hexadecanal is prepared by the dichromate oxidation of [1-$^{14}$C]hexadecan-1-ol, according to a microscale modification of the method of Pletcher and Tare (*Tet. Lett.* (1978) 1601–1602). The product is purified by preparative silica TLC, and stored as a hexane solution at −70° C. until use.

B. Assay for Reductase Activity in a Microsomal Membrane Preparation

1. Assay 1: Reductase activity in a microsomal membrane preparation is measured by incubation of 20 μM [1-$^{14}$C]acyl-CoA (usually tetracosenoyl-CoA, sp. act. 2–5 Ci/mol) with the sample to be assayed and 2 mM NADPH, in a total volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as referred to hereafter is added from a 1 M stock solution adjusted to pH 7.5).

The assay is started by the addition of acyl-CoA substrate and the incubation is carried out at 30° C. for one hour. The assay is terminated by placing the assay tube on ice and immediately adding 0.25 ml isopropanol:acetic acid (5:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Six ml of hexane/isopropanol (3:2, v/v) is added to the terminated assay. The sample is vortexed, 2 ml of aqueous sodium sulphate solution (5.5% w/v) is added, and the sample is again vortexed.

2. Assay 2: Reductase activity in a microsomal membrane preparation is measured by incubation of 20 μM [1-$^{14}$C]acyl-CoA (usually tetracosenoyl-CoA, sp. act. 2–5 Ci/mol) with the sample to be assayed and 2 mM NADPH, in a tonal volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as refered to hereafter is added from a 1 M stock solution adjusted to pH 7.5). If it is desired to inhibit an acyl CoA: alcohol acyl transferase activity which is also present in the membrane preparation (and which consumes the product of the reductase reaction), 0.3% w/v CHAPS is included in the assay mixture. This concentration of CHAPS has a minimal effect on the reductase enzyme but completely inhibits the acyl transferase reaction, thus simplifying quantitation of the reductase activity.

The assay is started by the addition of acyl-CoA substrate and the incubation is carried out at 30° C. for one hour. The assay is terminated by placing the assay tube on ice and immediately adding 0.25 ml isopropanol:acetic acid (4:1 v/v). Unlabeled wax esters (25 μg), oleyl alcohol (50 μg), and oleic acid (50 μg) are added as carriers. The $^{14}$C] lipids are extracted by the scaled-down protocol of Hara and Radin (*Anal. Biochem.* (1978) 90:420). Four ml of hexane/isopropanol (3:2, v/v) is added to the terminated assay. The sample is vortexed, 2 ml of aqueous sodium sulphate solution (6.7% w/v) is added, and the sample is again vortexed.

C. Assay for Solubilized Reductase Activity

For assaying solubilized reductase activity, several changes, including the addition of salt for enzyme activation, are required. The assay buffer for a solubilized reductase assay is as indicated above for the microsomal membrane preparation assay, with the following changes:

a. NaCl is added to a final concentration of between 0.3 and 0.5 M, b. EDTA is included at ~1 mM, and c. the enzyme sample to be assayed, which typically contains 0.75% CHAPS, is diluted to ≦0.3% (the CMC for CHAPS is ~0.5%).

D. Analysis of Assay Products

For analyzing the products of either the microsomal membrane preparation reductase assay or the solubilized reductase assay, two protocols have been developed. One protocol, described below as "extensive assay" is more timeconsuming, but yields more highly quantitative results. The other protocol, described below as "quick assay" also provides a measure of reductase activity, but is faster, more convenient, and less quantitative.

1. Extensive Analysis: Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of heptane, and an aliquot is assayed for radioactivity by liquid scintillation counting. The remainder of the sample can be used either for TLC analysis of the labeled classes, or for derivatization to cleave the wax esters, and thereby give a measure of total alcohol produced.

For lipid class analysis the sample is applied to a silica TLC plate, and the plate is developed in hexane/diethyl ether/acetic acid (such as 80:20:1 or 70:30:1 v/v/v). The distribution of radioactivity between the lipid classes, largely wax esters (when ligase is present, as in the microsomal membrane preparation assay), free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis.

For cleavage of the wax esters, a scaled down protocol based on the Grignard derivatization protocol of Pina et (*Lipids* (1987) 22:358–361) is used. The sample, plus 200 μg of carrier wax esters, is dried down in a glass tube fitted with a teflon-lined screw cap. Dry diethyl ether ethyl acetate (3 μl), and 3 M ethyl magnesium bromide in diethyl ether (0.1 ml) are added sequentially. The sample is vortexed and allowed to stand at room temperature for at least 2 hours, after which water-saturated diethyl ether is carefully added to destroy excess reagent. Two ml each of 1 M HCl and hexane are added and the tube is vortexed. The upper organic phase is washed with water (2×2 ml) and evaporated to dryness in the presence of 50–100 μl of ethanol.

The sample is resuspended in 50–100 μl of hexane and applied to a TLC plate. Both normal and reversed-phase TLC systems have been used for the analysis. Normal phase TLC uses a silica TLC plate, developed with hexane/diethyl ether/acetic acid (70:30:2 v/v/v). The reversed phase system uses C18 plates developed in methanol.

2. Quick Analysis: Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in heptane and spotted on TLC plates and developed and scanned as described for the detailed assay. In this manner the percentage of the total counts which are incorporated into alcohol is determined.

Example 2-Characterization of Jojoba Acyl-CoA Reductase

Methods to obtain jojoba protein preparations having reductase activity and results of studies of this enzymatic activity are presented.

A. Seed Development and Acyl-CoA Reductase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Acyl-CoA reductase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for acyl-CoA reductase activities as measured in either a cell free homogenate or a membrane fraction, indicate a large induction in reductase activity which peaks at approximately 115 days after anthesis. Embryos for enzymology studies were thus harvested between about 90 to 110 days postanthesis, a period when the reductase activity is high, lipid deposition has not reached maximum levels, and the seed coat is easily removed. The highest rate of increase of reductase activity is seen between days 80 and 90 postanthesis. Embryos for cDNA library construction were thus harvested between about 80 to 90 days postanthesis when presumably the rate of synthase of reductase protein would be maximal. Correspondingly, the level of mRNA encoding acyl-CoA reductase would be presumed to be maximal at this stage.

B. Fractionation Studies

Early attempts to fractionate jojoba embryo samples resulted in variable distribution of reductase activity in the fat pad, supernatant and particulate fractions resulting from centrifugation. A large number of treatments to potentially affect the distribution of activity were tested, such as sonication, floatation gradients, and the addition of various agents to the extraction buffer. The inclusion of salts in the extraction buffer resulted in the greatest improvement in recovery of ligase activity in the supernatant fraction upon centrifugation at 100,000×g for one hour. The extraction buffer consists of 3 M NaCl, 0.3 M sucrose, 100 mM HEPES, 2 mM DTT, and the protease inhibitors, 1 mM EDTA, 0.7 μg/ml leupeptin, 0.5 μg/ml pepstatin and 17 μg/ml phenylmethanesulfonyl fluoride (PMSF).

C. Microsomal Membrane Preparations

Particles having high levels of reductase activity can be obtained from the supernatant fraction described above either by dialysis followed by centrifugation at 100,000×g or by ammonium sulphate fractionation. The dialysis method is described in detail in Example 3. Further analysis of these particles having reductase activity such as density gradient centrifugation, gel permeation chromatography, and protein/phospholipid analysis establishes that these particles represent a membrane fraction. This membrane preparation also has high cytochrome C reductase activity, which activity is used as a marker for endoplasmic reticulum (ER) membranes. These studies thus establish that the reductase protein is associated with membranes.

For ammonium sulphate fractionation, the 100,000×g supernatant is obtained from jojoba embryos essentially as described in Example 3. An equal volume of ammonium sulphate solution (33.2 g/100 ml) is slowly added to the supernatant fraction (with stirring) to bring the ammonium sulphate concentration to 30%, a concentration that will effectively precipitate the reductase enzyme. Following 30 additional min. of stirring, the suspension is centrifuged at 26,000×g for 30 min., and the pellet resuspended in one tenth of the volume of the first supernatant fraction, S1, using a solution consisting of 25 mm HEPES, 1 M NaCl, 1 mM DTT, 0.1 mM PMSF. The suspension is centrifuged at 100,000×g for one hour, and the resulting pellet resuspended in 25 mM HEPES, 10% glycerol (again at 1/10th of the S1 volume). Centrifugation of this suspension at 100,000×g yields the washed microsomal pellet, P4, which is resuspended in 1/20th of the S1 volume of 25 mM HEPES, 10% glycerol yielding a protein concentration of about 3-4 mg/ml. Aliquots are frozen at −70° C. for later use.

D. Study Of Membrane Association of Reductase Activity

The Triton X114 phase fractionation procedure described by Bordier (*J. Biol. Chem.* (1981) 256:1604–1607) is used to determine whether the jojoba reductase is an integral membrane protein, or is more loosely associated with the membrane layer (more highly hydrophillic proteins). This technique essentially involves incubation of the membranes with 1% Triton X114 on ice followed by raising the temperature of the mixture above the cloud point of the detergent under these conditions (the cloud point is the temperature at which very large micelles begin to spontaneously form, for 1% Triton X114 this is ~20° C.). Upon centrifugation, two distinct phases can be observed, a lower detergent rich phase and an upper detergent depleted phase (refered to here as the aqueous phase). Integral membrane proteins have been shown to preferentially partition into the detergent rich phase while more highly hydrophilic proteins are recovered in the aqueous phase. When jojoba membrane preparations are subjected to this Triton X114 phase fractionation protocol, reductase activity is associated with the detergent enriched phase and no reductase activity is detected in the aqueous phase. This is evidence that the reductase enzyme is an integral membrane protein.

E. Further Characterization of Reductase Enzyme

The microsomal membrane preparation described above is used for further characterization of the reductase enzyme. The reductase enzyme was shown to be active over the range of pH 5–9. Characterization experiments were conducted at pH 7.5, which is close to the presumed physiological pH of the cytoplasm.

1. Salt Effects: A variety of salts were examined for their effect on reductase activity using a standard concentration of 0.5 M for monobasic salts. Salts with divalent cations or anions were examined at 0.167 M to give the same ionic strength as the 0.5 M monobasic salts and also at 0.5 M. Up to 15-fold stimulation is observed with the addition of 0.5 M NaCl. Other salts, both monovalent and divalent (such as LiCl, KCl, MgCl$_2$, CaCl$_2$ and Na$_2$SO$_4$) were also shown to stimulate reductase activity, although generally to a lesser degree as compared to the NaCl stimulation. Strongly chaotropic salts, KSCN and NaSCN gave no stimulation or marginal stimulation of reductase activity.

2. Other Effectors: Dithiothreitol (DTT) was found to be stimulatory to reductase activity, but not obligatory, while ethylenediaminetetraacetic acid (EDTA) gave some stimulation, with the optimum concentration being 2.5 mM. A small stimulation of activity was observed at low (0.02–0.075 mg/ml) BSA (bovine serum albumin) concentrations, while inhibition of activity was observed at BSA concentrations at and above 0.2 mg/ml.

Earlier observations that the acyl-CoA reductase is an NADPH specific activity (Pollard et al., supra) were confirmed. No NADH-dependent activity was measurable above background (<2% of the NADPH-dependent activity). Also, both water-soluble end-products of the reductase reaction, CoA and NADP+, give significant inhibition of activity (at millimolar concentrations), while NADH and NAD+ have marginal effects on activity.

3. Substrate Specificity: The thioesters of various chain length fatty acids, acyl-ACPs and acyl-CoAs, were compared as substrates for the reductase enzyme. Tests were conducted at substrate concentrations of 10 μM, as the tetracosenoyl-CoA (24:1-CoA) substrate shows strong substrate inhibition at greater concentrations. NaCl concentration in these assays is 0.5 M. Results of the substrate specificity experiment are presented in Table 1 below.

TABLE 1

| | Acyl Specificity of the Reductase | |
|---|---|---|
| | Reductase Activity (pmoles/min/μl) | |
| Acyl Group | Acyl-ACP (10 μM) | Acyl-CoA (10 μM) |
| 12:0 | <0.01 | <0.15 |
| 16:0 | 2.9 | <0.4 |
| 18:0 | — | 1.4 |
| 18:1 | 1.05 | 0.75 |
| 20:1 | — | 1.0 |
| 22:1 | — | 1.0 |
| 24:1 | — | 19.9 |

Tetracosenoyl-CoA has the highest substrate activity of those tested, and is thus used for reductase assays in further enzyme purification and characterization experiments. Of interest, palmitoyl-CoA (C16:0-CoA) and palmitoyl-ACP (C16:0-ACP) were directly compared as substrates. The activity towards palmitoyl-CoA was barely above background, while activity towards palmitoyl-ACP was high. Previously, stearoyl-ACP (C18:0-ACP) was shown to have activity as a substrate (Pollard et al., supra).

Also of interest, although palmitoyl-CoA appears to be a poor substrate for the reductase enzyme, in a competitive inhibition experiment conducted using unlabelled palmitoyl-CoA (0–30 μM) and [1-14C]tetracosenoyl-CoA (20 μM), 50% inhibition of reductase activity towards tetracosenoy-CoA occurred at 5 μM palmitoyl-CoA. Thus, although palmitoyl-CoA is a poor substrate under the assay conditions, it is an effective inhibitor. 4. Reductase Inhibitor Assays: Several known inhibitors of other types of reductase proteins were tested for their effect on the jojoba acyl-CoA reductase activity. Mevinolin, which is a strong inhibitor of HMG-CoA reductase (3-hydroxyl-3-methylglutaryl-coenzymeA reductase), only had an effect at relatively high concentrations (100 μM) compared to the concentrations inhibitory to HMG-CoA reductase (Ki of approximately 1 nM). Cerulinen is well known to covalently bind to β-ketoacyl thioester synthases, but has no strong inhibitory effect on the jojoba acyl-CoA reductase.

Sulphydryl blocking agents were also screened for their effect on reductase activity. N-ethylmaleimide was shown to strongly inhibit activity, while para-hydroxymercuribenzoate also had some inhibitory effect, and iodoacetamide had no effect. This evidence leads to the conclusion that the acyl-CoA reductase has an essential sulphydryl group that shows considerable selectivity towards various sulphydryl blocking reagents.

Example 3-Purification of Acyl-CoA Reductase

Methods are described which may be used for isolation of a jojoba membrane preparation having reductase activity, solubilization of reductase activity and further purification of the reductase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3 M NaCl, 0.3 M sucrose, 100 mM HEPES, 2 mM DTT, and the protease inhibitors, 1 mM EDTA, 0.7 μg/ml leupeptin, 0.5 μg/ml pepstatin and 17 μg/ml PMSF. A cell free homogenate (CFH) is formed by dispersing the powdered embryos in the buffer with a Polytron tissue homogenizer for approximately 30 seconds. The homogenate is filtered through three layers of Miracloth (CalBioChem, LaJolla, Calif.) and the filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1 M NaCl, 100 mM HEPES, 2 mM DTT and 1 mM EDTA. The dialyzate is centrifuged at 200,000×g for one hour to yield a pellet, DP2. The pellet is suspended in 25 mM HEPES (pH7.5), 10% (w/v) glycerol, 1 mM EDTA and 0.5 M NaCl at approximately 1/20 of the original CFH volume, to yield the microsomal membrane preparation.

Activity is assayed as described in Example 1. Recovery of acyl-CoA reductase activity is estimated at approximately 30% of the original activity in the cell free homogenate. Acyl-CoA reductase activity in this preparation is stable when stored at −70° C.

B. Solubilization Of Reductase Protein

Solid CHAPS (3-[(3-cholamidopropyl)-dimethylammonio]-1-propanesulfonate) is added to the microsomal membrane preparation to yield a final concentration of 2% (w/v). The sample is incubated on ice with a slow rocking motion for approximately one hour and then diluted with 25 mM HEPES (pH7.5), 10% glycerol, 0.34 M NaCl, 1 mM EDTA to lower the CHAPS concentration to 0.75% and the NaCl to approximately 0.4 M. The sample is then centrifuged at 200,000×g for one hour and the supernatant recovered and assayed for reductase activity as described in Example 1. Typically, 85% of the reductase activity from the microsomal membrane preparation is recovered in the supernatant fraction. The solubilized reductase activity is stable when stored at −70° C.

C. Blue A Column Chromtography

A column (1.8× ~10 cm) with a bed volume of approximately 25 ml is prepared which contains Blue A (Cibacron Blue F3GA; Amicon Division, W. R. Grace & Co.), and the column is equilibrated with Buffer A (25 mM HEPES (pH7.5), 20% (w/v) glycerol, 0.75% CHAPS, 1 mM EDTA) containing 0.4 M NaCl. The solubilized reductase preparation described above is loaded on to the Blue A column.

The column is washed with several column volumes of Buffer A containing 0.4 M NaCl and is then washed further with Buffer A containing 0.5 M NaCl. Greater than 90% of the reductase activity binds to the column, while greater than 85% of other protein passes through. Reductase activity is eluted from the column with Buffer A containing 1.0 M NaCl. Fractions are collected and assayed for reductase activity as described in Example 1. Fractions containing reductase activity are pooled and stored at −70° C. Typically, 30–50% of the loaded reductase activity is recovered by elution with the 1.0 M NaCl buffer.

D. Size Exclusion Chromatography

The pooled active fractions from the Blue A column are concentrated ~10 fold via ultrafiltration in a pressure cell fitted with a YM30 membrane (Amicon Division, W. R. Grace). Typically, the activity is eluted from the BlueA column in ~90 ml and concentrated to ~8 ml and applied to two Sephacryl S100 columns as follows. Columns (2.5×75 cm) are packed with S100HR medium (Pharmacia LKB Biotechnology, Piscataway, N.J.) and equilibrated with Buffer A containing 0.5 M NaCl. The columns are size calibrated with the following protein standards: bovine serum albumin (66 kD), carbonic anhydrase (29 kD), cytochrome C (12.4 kD), and blue dextran (used to determine the void volume). A four ml aliquot of the concentrated sample is applied to each of the S100 columns, which are developed at a linear flow rate of approximately 17 cm/hr. Fractions are collected for ~4 hours and the reductase activity in the fractions is measured as described in Example 1.

Greater than 60% of loaded activity is recovered in one main peak which elutes at an apparent molecular mass of approximately 49 kD. The volume of the pooled active fractions is ~30–35 ml/column.

E. Affinity Chromatography

A column (1.5 cm× ~2 cm) is packed with palmitoyl-CoA agarose (Sigma Chemical Co., St. Louis, Mo.) and equilibrated with Buffer B (Buffer A containing 0.1 M NaCl). Pooled active fractions from the gel filtration columns are concentrated ~16 fold via ultrafiltration as described above. The NaCl level in the concentrated sample is reduced from 0.5 M to ~0.1 M by dilution with Buffer A. The diluted sample is applied to the column which is then washed with several column volumes of Buffer B. The column is then washed with 10 ml of Buffer B containing 15 mM NADH, followed by further washing with Buffer B. Reductase activity is eluted by passing 15 ml of 15 mM NADPH in Buffer B through the column. Typically, the material from one gel filtration column at a time is processed on the affinity column, and greater than 70% of the activity applied to the column is recovered by elution with NADPH. The active fractions are pooled and analyzed for reductase activity, protein concentration and polypeptide composition. Protein concentrations are estimated using a commercially available kit (Bio-Rad Laboratories, Inc., Richmond, Calif.) based on the dye binding method described by Bradford (*Analy. Biochem.* (1976) 72:248–254). BSA is used as the reference protein.

F. Purification Table

Protein recovery and reductase activity at each step in a typical purification experiment are presented in Table 2 below.

TABLE 2

Purification of Jojoba Reductase

| Purification Step | Enzyme Activity (nmol/min) | Yield (%) | Protein (mg) | Specific Activity (nmol/min/mg) | Purification (fold) |
|---|---|---|---|---|---|
| Crude Homogenate | 380 | | | | |
| First Supernatant | 164 | 100 | 1172 | 0.1 | 1.0 |
| Microsomal Membranes | 82 | 50 | 77.5 | 1.1 | 7.6 |
| Solubilized Fractions | 64 | 39 | 68.5 | 0.9 | 6.7 |
| Blue A Agarose | 39 | 23.8 | 2.2 | 18.1 | 130 |
| Sephacryl-S100 | 13.4 | 8.2 | 1.7 | 8.1 | 58 |
| Palmitoyl CoA Agarose | 4.7 | 2.9 | 0.2 | 21.9 | 156 |

G. SDS PAGE Analysis

Polypeptide composition of the sample is analyzed by SDS PAGE (Laemmli, U. K. (1970) *Nature* (London) 227:680–685). The samples are prepared for electrophoresis by adding SDS and dithiothreitol from stock solutions to a final concentration of 2% and 30 mM, respectively. Approximately 50 μl of the sample is loaded onto the well of an acrylamide gel having a 12% separating gel (NOVEX, San Diego, Calif.). Molecular mass standards were purchased from Bio-Rad Laboratories. Protein is detected by silver staining (Blum et al., *Electrophoresis* (1987) 8:93–99).

Two prominent polypeptide bands having apparent molecular masses of approximately 52 and 54 kD are detected in the active sample from the affinity column which together represent >95% of the protein in this preparation. Further analyses of these samples using a protein size marker system that includes a 55 kD protein standard results in alternative molecular mass estimates of 54 and 56 kD. As the apparent size of the reductase enzyme in the native state is approximately 49 kD (as determined by size exclusion chromatography and described above), these bands likely represent related forms of the reductase enzyme rather than two different subunits of one enzyme.

H. Blotting Proteins to Membranes

The above described reductase polypeptides are further isolated for amino acid sequencing by transfer of these proteins to either nitrocellulose or PVDF, either Immobilon-P (Millipore; Bedford, Mass.) or ProBlott (Applied Biosystems; Foster City, Calif.), membranes following SDS-PAGE. Nitrocellulose is preferred when proteins will be subsequently enzymatically digested, while PVDF is useful for N-terminal sequencing methods and for sequencing of peptides resulting from cyanogen bromide digestion.

1. Blotting to Nitrocellulose: When protein is electroblotted to nitrocellulose, the blotting time is typically 1–5 hours in a buffer such as 25 mM Tris, 192 mM glycine in 5–20% methanol. Following electroblotting, membranes are stained in 0.1% (w/v) Ponceau S in 1% (v/v) acetic acid for 2 minutes and destained in 2–3 changes of 0.1% (v/v) acetic acid, 2 minutes for each change. These membranes are then stored wet in heat-sealed plastic bag at −20° C. If time permits, blots are not frozen but used immediately for digestion to create peptides for determination of amino acid sequence as described below.

2. Blotting to PVDF: When protein is electroblotted to Immobilon P PVDF, the blotting time is generally about 1–2 hours in a buffer such as 12.5 mM Tris/5 mM glycine in 10% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below in Example 4A.

Example 4-Determination of Amino Acid Sequence

In this Example, methods for determination of amino acid sequences of plant proteins associated with acyl-CoA reductase activity are described.

A. CyanoGen Bromide Cleavage of Protein and Separation of Peptides

Cyanogen bromide cleavage is performed on the protein of interest using the methodology described in the Probe-Design Peptide Separation System Technical Manual from Promega, Inc. (Madison, Wis.). The reductase proteins are blotted to a PVDF membrane as described above. Protein bands are cut from the blot, placed in a solution of cyanogen bromide in 70% (v/v) formic acid, and incubated in this solution overnight at room temperature. Following this incubation the cyanogen bromide solutions are removed, pooled and dried under a continuous nitrogen stream using a Reacti-Vap Evaporator (Pierce, Rockford, Ill.). Additional elution of cyanogen bromide peptides may be conducted to ensure complete removal, using a peptide elution solvent such as 70% (v/v) isopropanol, 0.2% (v/v) trifluoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 μl of HPLC grade water is then added to the dried peptides and the water removed by evaporation in a Speed-Vac (Savant, Inc., Farmingdale, N.Y.).

Peptides are separated using a Tris/Tricine SDS-PAGE system similar to that described by Schägger and yon Jagow (*Anal. Biochem.* (1987) 166:368–379). Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3X 2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

B. Protease Digestion and Separation of Peptides

Proteins blotted to nitrocellulose may be subjected to digestion with proteases in order to obtain peptides for sequencing. The method used is that of Aebersold, et al. (PNAS (1987) 84:6970). Bands of the reductase proteins, and also an equal amount of blank nitrocellulose to be used as a control, are cut out of the nitrocellulose membrane and washed several times with HPLC grade water in order to remove the Ponceau S. Following this wash, 1.0 ml of 0.5% polyvinylpyrrolidone (PVP-40, Aldrich, Milwaukee, Wis.) in 0.5% acetic acid is added to the membrane pieces and this mixture is incubated for 30 minutes at 37° C. In order to remove the PVP-40 completely, nitrocellulose pieces are washed with many volumes of HPLC grade water (8×5 ml), checking the absorbance of the washes at 214 nm on a spectrophotometer. Also, PVP-40 is more easily removed if bands are not cut into small pieces until after PVP-40 treatment and washing. These two modifications eliminate interference problems with the PVP-40.

The pieces are then suspended in an appropriate digest buffer, for example trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5–10% (v/v). Protease are diluted in digest buffer and added to the digest mixture, typically at a ratio of 1:10 (w/w) protease to protein. Digests are incubated 18–24 hours. For example, trypsin digests are incubated at 37° C. and endoproteinase gluC digests are incubated at room temperature. Similarly, other proteases may be used to digest the reductase proteins, including lysC and aspN. While the individual digest buffer conditions may be different, the protocols for digestion, peptide separation, purification and sequencing are substantially the same as those described for digestion with trypsin and gluC.

Following overnight incubation, digest reactions are stopped by the addition of 10 μl 10% (v/v) trifluoroacetic acid (TFA) or 1μl 1 100% TFA. The digest mixture is removed from the nitrocellulose pieces, the nitrocellulose pieces are washed with 1–5 100 μl volumes of digest buffer with 5–10% acetonitrile, and these volumes are concentrated to a volume of less than 100 μl in a Speed-Vac. The peptides are separated on a Vydac reverse phase C18 column (2.1 mm × 100 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH2.2; Buffer B: 70% acetonitrile in 0.1 mM sodium phosphate, pH2.2. A 3-step gradient of 10–55% buffer B over two hours, 55–75% buffer B over 5 minutes, and 75% buffer B isocratic for 15 minutes at a flow rate of 50 μl/minute is used. Peptides are detected at 214 nm, collected by hand, and then stored at −20°C.

C. N-terminal Sequencing Of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5–30 pmoles), the 477A conversion cycle and the 120A analyzer as described by Tempst and Riviere (Anal. Biochem. (1989) 183:290).

D. Amino Acid Sequence of Reductase Peptides

Purified reductase preparations are applied to SDS-PAGE to separate the 54 and 56 kD proteins. The separated material is transferred to a nitrocellulose type of membrane (Immobilon N) and stained with Ponceau Red to locate the bands. Excised portions of the blots, containing either the 56 or the 54 kD protein, are treated with trypsin and the tryptic peptides separated by reverse phase HPLC. Sequence information obtained from several peptides (SEQ ID NOS: 1–18) from each reductase protein is presented below in Table 3.

TABLE 3

Peptide Sequences of 54 and 56kD Reductase Proteins 56 kD Reductase Peptides
1) AILVTGATGSLAK (SEQ ID NO: 1)
2) LQNExFGKELFK (SEQ ID NO: 2)
3) VTVVPGDITGEDL (SEQ ID NO: 3)
4) LGLDINVEK (SEQ ID NO: 4)
5) TIDNVPVYYGK (SEQ ID NO: 5)
6) YVEPVTYHVGSSAANPM (SEQ ID NO: 6)
7) LSALPEMAHR (SEQ ID NO: 7)
8) LVDIYK (SEQ ID NO: 8)
9) EGIVEADMFYFD (SEQ ID NO: 9)
10) AINWEDYFLKTxFPGVVExVL (SEQ ID NO: 10)

54 kD Reductase Peptides
1) AILVTGATGSLAK (SEQ ID NO: 11)
2) LGLDINVEK (SEQ ID NO: 12)
3) TIDNVPVYYG (SEQ ID NO: 13)
4) YVEPVTYxVGSSAAN (SEQ ID NO: 14)
5) LVDIYKp (SEQ ID NO: 15)
6) EGIVEADMFYF (SEQ ID NO: 16)

TABLE 3-continued

Peptide Sequences of 54 and 56kD Reductase Proteins

7) AINWEDYFL (SEQ ID NO: 17)
8) THFPGVVEHVL (SEQ ID NO: 18)

Peptide sequences are listed using the standard one letter code for amino acids. An "x" indicates that the amino acid at that position was not identified. Amino acid designations which appear in small letters indicate that the identification was tentative for that amino acid.

The similarity of the two reductase proteins is evident from the above peptide sequences. All the peptides from the 54 kD protein are also found in the sequenced 56 kD peptides. There is one discrepancy between the determined amino acid sequences and that reductase amino acid sequence deduced from the cDNA encoding the 56 kD reductase (FIG. 1 (SEQ ID NO: 19)). Amino acid 460 is a serine according to cDNA sequence data. Information from 54 and 56 kD peptides 6 and 9, respectively, indicate that a glycine is at this position.

E. Western Analysis

A portion of the reductase cDNA (Example 5) which encodes amino acids 167–235 of the reductase 56 kD protein (see FIG. 1) is ligated into an E. coli pGEX expression vector (AMRAD; Burwood, Victoria; Australia) in frame for expression of the reductase peptide from the Taq promoter. The resulting construct is used to transform E. coli cells for production of the reductase peptide. The 69 amino acid peptide produced in this manner is purified (Smith et al. (1988) Gene 67:31–40) and used to obtain polyclonal antibody to the reductase peptide.

A Western blot of a purified reductase preparation containing the 56 and 54 kD bands and a jojoba cell free homogenate (Example 3A) is prepared for analysis of the reductase preparations using the above described antibody preparation. The 56 kD band is detected in both the cell free homogenate and the purified reductase preparations, while the 54 kD band is detected only in the purified reductase preparation. These results suggest that the 54 kD band observed in the purified reductase preparation is a breakdown product of the 56 kD protein that results from the reductase purification procedure.

Furthermore, Southern blot analysis of restriction enzyme digested jojoba genomic DNA, using four different restriction enzymes, results in detection of one major band and one minor band which hybridize to the reductase cDNA (Example 5) probe.

Example 5-Jojoba Reductase cDNA

A. Jojoba RNA Isolation

RNA is isolated from polyribosomes by a method initially described by Jackson and Larkins (*Plant Physiol.* (1976) 57:5–10) as modified by Goldberg et al. (*Developmental Biol.* (1981) 83:201–217). In this procedure all steps, unless specifically stated, are carried out at 4° C. 10 gm of jojoba embryos collected at 80–90 days post-anthesis are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 05% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8 M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5ml of resuspension buffer (40 mM Tris pH 9.0, 5 mM EGTA, 200 mM KCl, 30 mM MgCl2, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-lauryl-sarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000×g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5 M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

B. cDNA Library Construction in a Plasmid Vector

Polyadenylated RNA is used to construct a cDNA library in the plasmid cloning vector pCGN1703, derived from the commercial cloning vector Bluescribe M13- (StraEagene Cloning Systems; San Diego, Calif.), and made as follows. The polylinker of Bluescribe M13- is altered by digestion with BamHI, treatment with mung bean endonuclease, and blunt-end ligation to create a BamHI-deleted plasmid, pCGN1700. pCGN1700 is digested with EcoRI and SstI (adjacent restriction sites) and annealed with a synthetic linker having restriction sites for BamHI, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHi sticky-end, recognition sequences for restriction enzymes NotI, EcoRI and SstI, and a 3' C-tail end. Following ligation and repair the circular complexes are transformed into *E. coli* strain DH5α (BRL, Gaithersburg, Md.) to generate the cDNA library. The jojoba embryo cDNA bank contains between approximately $1.5 \times 10^6$ clones with an average cDNA insert size of approximately 500 base pairs.

C. cDNA Library Construction in a Lambda Vector

Jojoba polyadenylated RNA is also used to construct a cDNA library in the cloning vector λZAPII/EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately $1 \times 10^6$ clones with an average cDNA insert size of approximately 400 base pairs.

D. Isolation Of Reductase cDNA

PCR techniques with primers designed from reductase peptide sequences are utilized to generate an approximately 1 kb portion of a reductase nucleic acid sequence for screening the jojoba library in the pCGN1703 bacterial vector.

The library is screened using techniques known in the art, such as described in Maniatis et al. (supra). A clone, pCGN7571, for the 56 kD reductase protein is obtained and the DNA sequence determined. Nucleic acid and deduced amino acid sequences of pCGN7571 (SEQ ID NO:19) are presented in FIG. 1.

E. Expression of Reductase cDNA in *E. coli* pCGN7571 is in vitro mutagenized to introduce an NdeI site at the first ATG of the reductase coding sequence and a BglII site immediately upstream of the NdeI site. BamHI linkers are introduced into the SphI site downstream of the reductase coding region. The 1.5 kb BglII-BamHI fragment is gel purified and cloned into BglII-BamHI digested pCGN3686 (see below), resulting in pCGN7582.

pCGN3686 is a cloning vector derived from Bluescript KS+ (Stratagene Cloning Systems; San Diego, Calif.), but having a chloramphenicol resistance gene and a modified linker region. The source of the chloramphenicol resistance gene, pCGN565 is a cloning vector based on pUC12-cm (K. Buckley Ph.D. Thesis, Regulation and expression of the phi X174 lysis gene, University of California, San Diego, 1985), but containing pUC18 linkers (Yanisch-Perron, et al., *Gene* (1985) 53:103–119). pCGN565 is digested with HhaI and the fragment containing the chloramphenicol resistance gene is excised, blunted by use of mung bean nuclease, and inserted into the EcoRV site of Bluescript KS- (Stratagene: La Jolla, Calif.) to create pCGN2008. The chloramphenicol resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015. The linker region of pCGN2015 is modified to provide pCGN3686, which contains the following restriction digestion sites, 5' to 3' in the lacZ linker region: PstI, BglII, XhoI, HincII, SalI, HindIII, EcoRV, EcoRI, PstI, SmaI, BamHI, SpeI, XbaI and SacI.

As the BamHI site downstream of the reductase gene was destroyed during construction of pCGN7582, BamHI linkers are inserted into pCGN7582 at the XbaI vector site downstream of the reductase gene, and the NdeI-BamHI fragment containing the reductase gene cloned into BamHI-NdeI digested pET3A (Studier et al. (1990) *Methods Enzymol.* 185:60–89). This plasmid is designated pCGN7800. pCGN7800 is transformed into *E. coli* BL21 (Studier et al., supra), which has the T7 RNA polymerase under the control of an inducible promoter.

BL21 *E. coli* cells containing the reductase constructs BL21(pCGN7800), are compared to control BL21 cells having only the pET3A vector. Cultures are grown overnight in ECLB with 40 μg/ml carbenicillin, diluted 1/10 in fresh ECLB with 40 μg/ml carbenicillin and grown for 1 hour. IPTG is added to 1 mM and the cells are grown for 3 additional hours before harvesting. The cells are harvested by centrifugation and the cell pellet stored at −70° C. Cells are broken in a french press and the protein extract is assayed for reductase activity using the reductase assay described in Example 1C, except that the concentration of NADPH is increased from 2 mM to 5 mM. The assay products are analyzed as described in Example 1D. Thin layer chromatography (TLC) analysis of assay products of BL21(pCGN7800) cell extracts reveals alcohol formation, while the extracts from BL21(pET3A) control cells do not catalyze alcohol formation. In addition, SDS PAGE analysis of BL21(pCGN7800) and BL21(pET3A) cells reveals that the 56 kD protein is present in the BL21(pCGN7800) cells and absent from the BL21(pET3A) cells.

To determine if the reductase expressing *E. coli* cells are producing alcohol, total lipids are extracted from BL21(pCGN7800) cells and control cells by hexane:isopropanol (3:2) extraction (overnight on a shaker). The organic phase is evaporated to dryness and the lipids are dissolved in a small volume of hexane, analyzed by TLC, and visualized by iodine staining. This analysis indicates that lipids extracted from BL21(pCGN7800) cells contain alcohols, while the lipids extracted from the control cells do not.

To determine the carbon chain length of the alcohol produced in the BL21(pCGN7800) cells, the alcohol band is scraped from TLC plates and analyzed by reverse phase TLC and gas chromatography (GC). GC analysis is conducted as described by Pina et al. (*Lipids* (1987) 22:358–361) using a 30 m SUPEL-COWAX TM 10 (Supelco, Inc.; Bellefonte, Pa.) fused capillary column (0.32 mm internal diameter; 0.2 μm film thickness). The program parameters are as follows: 190° C. for 15 minutes followed by a 5° per minute temperature ramp to 250° C., hold at 250° C. for 3 minutes. In this manner, it is determined that 16:0 and 18:1 alcohols are the predominant alcohols produced in *E. coli* as the result of expression of the jojoba reductase.

Example 6-Plant Transformation with Reductase Constructs

A. Expression Constructs

Constructs for expression of reductase in plant cells using 5' and 3' regulatory regions from a napin gene, are prepared.

A napin expression cassette, pCGN1808, is described in copending U.S. patent application Ser. No. 07/550,804, and in Kridl et al. (*Seed Science Research* (1991)1:209–219), which are incorporated herein by reference. pCGN1808 is modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using in a Perkin Elmer/Cetus thermocycler according to manufacturer's specifications. The PCR fragment is subcloned as a blunt-ended fragment into pUC8 (Vieira and Messing (1982) *Gene* 19:259–268) digested with HincII to give pCGN3217. Sequenced of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

The reductase cDNA, pCGN7571, is digested with SphI (site in 3' untranslated sequence at bases 1594–1599) and a SalI linker is inserted at this site. The resulting plasmid is digested with BamHI and SalI and the fragment containing the reductase cDNA gel purified and cloned into BglII/XhoI digested pCGN3223, the napin cassette described above, resulting in pCGN7585.

A HindIII fragment of pCGN7586 containing the napin 5'/reductase/napin 3' construct is cloned into HindIII digested pCGN1578 (McBride and Summerfelt, supra), resulting in pCGN7586, a binary vector for plant transformation.

Plant transformation construct pCGN7589, also containing the jojoba reductase gene under expression of a napin promoter, is prepared as follows. An XhoI linker is inserted at the XbaI site of pCGN7582. The BglII-XhoI fragment containing the reductase gene is isolated and cloned into BglII-XhoI digested pCGN3223. The resulting plasmid, which lacks the 5' untranslated leader sequence from the jojoba gene, is designated pCGN7802. The napin/reductase fragment from pCGN7802 is excised with HindIII and cloned into HindIII digested pCGN1578 (McBride et al. supra) to yield pCGN7589.

pCGN7586 and pCGN7589 are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187) and used in plant transformation methods as described below.

B. Plant Transformation

Seeds of high erucic acid, such as cultivar Reston, and Canola-type varieties of *Brassica napus* are soaked in 95% ethanol for 2 minutes, surface sterilized in a 1.0% solution of sodium hypochlorite containing a drop of Tween 20 for approximately 30 minutes, and rinsed three times in sterile, distilled water. Seeds are then plated in Magenta boxes with 1/10 concentration of Murashige minimal organics medium (Gibco; Grand Island, N.Y.) supplemented with pyriodoxine (50 μg/l), nicotinic acid (50 μg/l), glycine (200 μg/l), and 0.6% Phytagar (Gibco) pH 5.8. Seeds are germinated in a cell culture room at 22°–24° C. in a 16 h photoperiod with cool fluorescent and red light of intensity approximately 45–55μ Einsteins per square meter per second ($\mu Em^{-2}S^{-1}$).

Hypocotyls are excised from 6–7 day old seedlings, cut into pieces approximately 2–4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1mg/l). In experiments where feeder cells are not used hypocotyl explants are cut and placed onto a filter paper disc on top of MS0/1/0 medium. All hypocotyl explants are preincubated on feeder plates for 24 h. at 22°–24° C. in continuous light of intensity 30 $\mu$Em$^{-2}$S$^{-1}$ to 65 $\mu$EM$^{-2}$S$^{-1}$.

Single colonies of *A. tumefaciens* strain EHA 101 containing a binary plasmid are transferred to 5 ml MG/L broth and grown overnight at 30° C. Hypocotyl explants are immersed in approximately 10 ml MG/L broth with bacteria diluted to $1 \times 10^8$ bacteria/ml and after approximately 10 minutes are placed onto feeder plates. Per liter MG/L broth contains 5 g mannitol, 1 g L-Glutamic acid or 1.15 g sodium glutamate, 0.25 g kH$_2$PO$_4$, 0.10 g NaCl, 0.10 g MGSO$_4$.7H$_2$O, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium (B5 salts and vitamins supplemented with 1 mg/l 2,4-D; 0.6% Phytagar) containing filter sterilized carbenicillin (500 mg/l, added after autoclaving) and kanamycin sulfate (Boehringer Mannheim; Indianapolis, Ind.) at concentrations of 25 mg/l.

After 3–7 days in culture at approximately 85 $\mu$EM$^{-2}$S$^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar).

Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

C. Analysis of Transformed Plants

Developing seeds from Arabidopsis plants transformed with the pCGN7586 napin/reductase construct, are analyzed for reductase activity as described in Example 1C. Out of fifteen plants analyzed, eleven were found to have reductase enzyme activity, with specific activities ranging from 5 to 30 pmol/min/mg protein. Western analysis demonstrates that the amount of reductase present in transgenic Arabidopsis embryos is approximately 0.01% of total protein. Lipids are extracted from mature seeds, derivatized (Browse et al. (1986) *Anal. Biochem.* 152:141–145) and analyzed for alcohol content by GC as described above. These analyses reveal the presence of 20:1 alcohol in 3 of the transformed Arabidopsis plants.

The above results demonstrate the ability to obtain solubilized seed-plant fatty acyl reductase protein which is active in the formation of a fatty alcohol. Methods to obtain the acyl reductase protein and amino acid sequences thereof are provided. In addition, reductase nucleic acid sequence is also provided. These nucleic acid sequences may be manipulated to provide for transcription of the sequences and/or expression of reductase proteins in host cells, which proteins may be used for a variety of applications, including production of fatty alcohols in plant cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent co those of ordinary skill in the art in light of the teaching of this invention that certain changes and modifications may be made thereto without departing from the spirit or scope of the appended claims.

What is claimed is:

1. A recombinant construct comprising a nucleic acid sequence which encodes a jojoba embryo long chain fatty acyl-CoA reductase wherein said reductase is active in the formation of a fatty alcohol from a fatty acyl substrate.

2. The recombinant construct of claim 1 wherein said reductase is active toward a fatty acyl substrate having a carbon chain of the formula $C_{2x}$ wherein X is selected from the group 8-12.

3. The recombinant construct of claim 1 wherein said reductase is NADPH-dependent.

4. The recombinant construct of claim 1 further comprising a 5' noncoding sequence which provides for at least transcription of said reductase encoding sequence in a plant or bacterial cell.

5. The recombinant construct of claim 1 further comprising a 5' noncoding sequence which provides for expression of said reductase encoding sequence in a plant or bacterial cell.

6. A plant or bacterial cell comprising a recombinant construct according to claim 1.

7. A plant cell comprising a recombinant construct according to claim 1.

8. A Brassica plant cell comprising a recombinant construct according to claim 1.

9. An *E. coli* cell comprising a jojoba embryo long chain fatty acyl-CoA reductase.

10. A method of producing a fatty acyl-CoA reductase in a plant or bacterial cell comprising the steps of
growing a plant or bacterial cell containing a recombinant construct,
said construct comprising a nucleic acid sequence which encodes a jojoba embryo long chain fatty acyl-CoA reductase wherein said reductase is active in the formation of a fatty alcohol from a fatty acyl substrate and wherein said reductase encoding sequence is under the control of regulatory elements functional in said plant or bacterial cell,
under conditions which will cause the expression of said reductase sequence.

11. The method of claim 10 wherein said cell is a seed plant embryo cell.

12. The method of claim 10 wherein said cell is a Brassica cell.

13. A method of producing a fatty alcohol in a plant or *E. coli* cell comprising the steps of
growing a plant or *E. coli* cell containing a recombinant construct,
said construct comprising a nucleic acid sequence which encodes a jojoba embryo long chain fatty acyl-CoA reductase wherein said reductase is active in the formation of a fatty alcohol from a fatty acyl substrate and wherein said reductase encoding sequence is under the control of regulatory elements functional in said plant or *E. coli* cell,
wherein said plant or *E. coli* cell is grown under conditions which will cause the expression of said reductase sequence,
and wherein said plant or *E. coli* cell contains a fatty acyl substrate of said reductase.

14. The method of claim 13 wherein said plant cell is a seed plant embryo cell.

15. The method of claim 13 wherein said plant cell is a Brassica cell.

16. The method of claim 13 wherein said plant cell is an Arabidopsis cell.

17. A recombinant construct according to claim 4 or 5 wherein said cell is an *E. coli* cell.

18. A cell according to claim 6 wherein said cell is an *E. coli* cell.

19. The method of claim 10 wherein said cell is an *E. coli* cell.

20. A recombinant construct comprising a nucleic acid sequence encoding a fatty acyl-CoA reductase active in the formation of a fatty alcohol from a fatty acyl substrate, wherein said nucleic acid sequence encodes a fatty acyl-CoA reductase protein having the amino acid sequence shown in FIG. 1.

21. The recombinant construct of claim 20 comprising a transcriptional initiation region functional in a plant cell, said nucleic acid sequence encoding a fatty acyl-CoA reductase, and a transcriptional termination region functional in a plant cell, wherein at least one of said transcriptional initiation and transcriptional termination regions is not naturally associated with said nucleic acid sequence encoding a fatty acyl-CoA reductase.

22. A vector comprising the recombinant construct of claim 20.

23. The vector of claim 22, wherein said vector further comprises a structural gene providing for selection of transformed cells.

24. A plant cell comprising a recombinant construct according to claim 20 or 21.

25. The method of claim 13 or 19 wherein said nucleic acid sequence encodes a fatty acyl-CoA reductase protein having the amino acid sequence shown in FIG. 1.

26. The method of claim 13 wherein said plant cell is a cruciferous plant cell.

* * * * *

UNITED STATES PATENT AND TRADEMARK OFFICE
CERTIFICATE OF CORRECTION

PATENT NO. : 5,370,996
DATED : December 6, 1994
INVENTOR(S) : Metz, James G.; Lassner, Michael W.

It is certified that error appears in the above-indentified patent and that said Letters Patent is hereby corrected as shown below:

On the title page, item [75] inventor, delete the line reading "Michael R. Pollard, Madison, Wisconsin".

Signed and Sealed this

Twenty-first Day of March, 1995

Attest:

BRUCE LEHMAN

Attesting Officer        Commissioner of Patents and Trademarks